(12) United States Patent
Sherry et al.

(10) Patent No.: US 7,484,305 B2
(45) Date of Patent: Feb. 3, 2009

(54) GAUGE FOR USE IN A SURGICAL PROCEDURE

(75) Inventors: Eugene Sherry, New South Wales (AU); Michael Egan, New South Wales (AU); Bob Lye, New South Wales (AU)

(73) Assignee: International Patent Owners (Cayman) Limited, Grand Cayman (KY)

( * ) Notice: Subject to any disclaimer, the term of this patent is extended or adjusted under 35 U.S.C. 154(b) by 0 days.

(21) Appl. No.: 10/578,993

(22) PCT Filed: Nov. 12, 2004

(86) PCT No.: PCT/AU2004/001568

§ 371 (c)(1),
(2), (4) Date: May 11, 2006

(87) PCT Pub. No.: WO2005/046475

PCT Pub. Date: May 26, 2005

(65) Prior Publication Data

US 2007/0051002 A1    Mar. 8, 2007

(30) Foreign Application Priority Data

Nov. 12, 2003   (AU)   .............................. 2003906238

(51) Int. Cl.
*G01C 9/12* (2006.01)
*A61B 5/103* (2006.01)

(52) U.S. Cl. ..................... 33/391; 33/512; 623/912; 606/102

(58) Field of Classification Search .................. 33/391, 33/392, 395, 397–399, 402, 365, 511, 512, 33/1 N, 1 BB, 281–283, 353, 534, 538; 623/912, 623/914; 606/130, 102
See application file for complete search history.

(56) References Cited

U.S. PATENT DOCUMENTS

| | | | | | |
|---|---|---|---|---|---|
| 1,003,863 | A | * | 9/1911 | Arnst | 33/395 |
| 1,409,833 | A | * | 3/1922 | Cook | 33/402 |
| 1,495,629 | A | * | 5/1924 | Andrew | 33/391 |
| 2,385,424 | A | * | 9/1945 | Shue et al. | 33/397 |

(Continued)

FOREIGN PATENT DOCUMENTS

GB    922007    3/1963

(Continued)

*Primary Examiner*—G. Bradley Bennett
*Assistant Examiner*—Amy Cohen Johnson
(74) *Attorney, Agent, or Firm*—The Webb Law Firm

(57) ABSTRACT

A gauge for use in a surgical procedure, including a body with a plumb bob mounted to the body. The plumb bob hangs from the body under the influence of a local gravitational field. More particularly, the plumb bob is rotatable relative to the body in both a first plane and a second plane, said planes being orthongonal to each other. In use, a connector allows the gauge to be connected to various surgical implements. The position of the indicator needle on the plumb bob is noted with reference to two sets of markings on the body to allow a surgeon to determine a first angle in a first plane and a second angle in a second plane. In one exemplary application of the invention, the first and second angles are anatomical angles associated with the surgical insertion of prosthetic components.

13 Claims, 32 Drawing Sheets

U.S. PATENT DOCUMENTS

| | | | |
|---|---|---|---|
| 2,554,133 A * | 5/1951 | Von Arx | 33/397 |
| 2,627,666 A * | 2/1953 | Levrero | 33/395 |
| 4,571,243 A * | 2/1986 | Froning et al. | 604/116 |
| 4,627,172 A * | 12/1986 | Afromowitz | 33/366.13 |
| 5,102,391 A | 4/1992 | Palestrant | |
| 5,122,145 A * | 6/1992 | Fishbane | 606/102 |
| 5,141,512 A * | 8/1992 | Farmer et al. | 606/87 |
| 5,191,714 A * | 3/1993 | Liu | 33/391 |
| 5,314,432 A * | 5/1994 | Paul | 606/130 |
| 6,049,989 A * | 4/2000 | Lee | 33/355 R |
| 6,302,890 B1 * | 10/2001 | Leone, Jr. | 606/91 |
| 6,361,506 B1 * | 3/2002 | Saenger et al. | 600/587 |
| 6,623,488 B1 * | 9/2003 | Leone, Jr. | 606/102 |
| 6,949,105 B2 * | 9/2005 | Bryan et al. | 606/130 |
| 7,051,451 B2 * | 5/2006 | Augostino et al. | 33/512 |
| 2005/0059978 A1 * | 3/2005 | Sherry et al. | 606/87 |
| 2006/0095047 A1 * | 5/2006 | de la Barrera | 606/102 |
| 2006/0184177 A1 * | 8/2006 | Echeverri | 606/91 |
| 2007/0051002 A1 * | 3/2007 | Sherry et al. | 33/397 |
| 2007/0083214 A1 * | 4/2007 | Duncan et al. | 606/102 |

FOREIGN PATENT DOCUMENTS

| | | |
|---|---|---|
| SU | 606578 | 4/1978 |
| SU | 988275 | 1/1983 |
| SU | 1090339 | 5/1985 |
| SU | 1378833 | 3/1988 |
| WO | WO 03/037192 | 5/2003 |

* cited by examiner

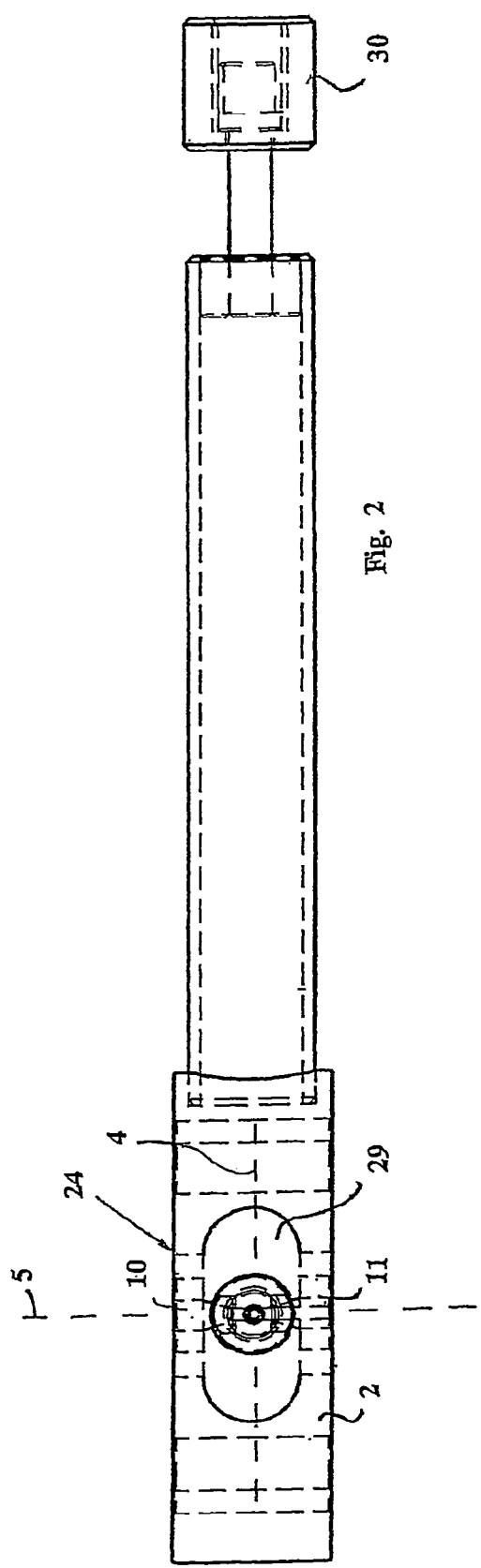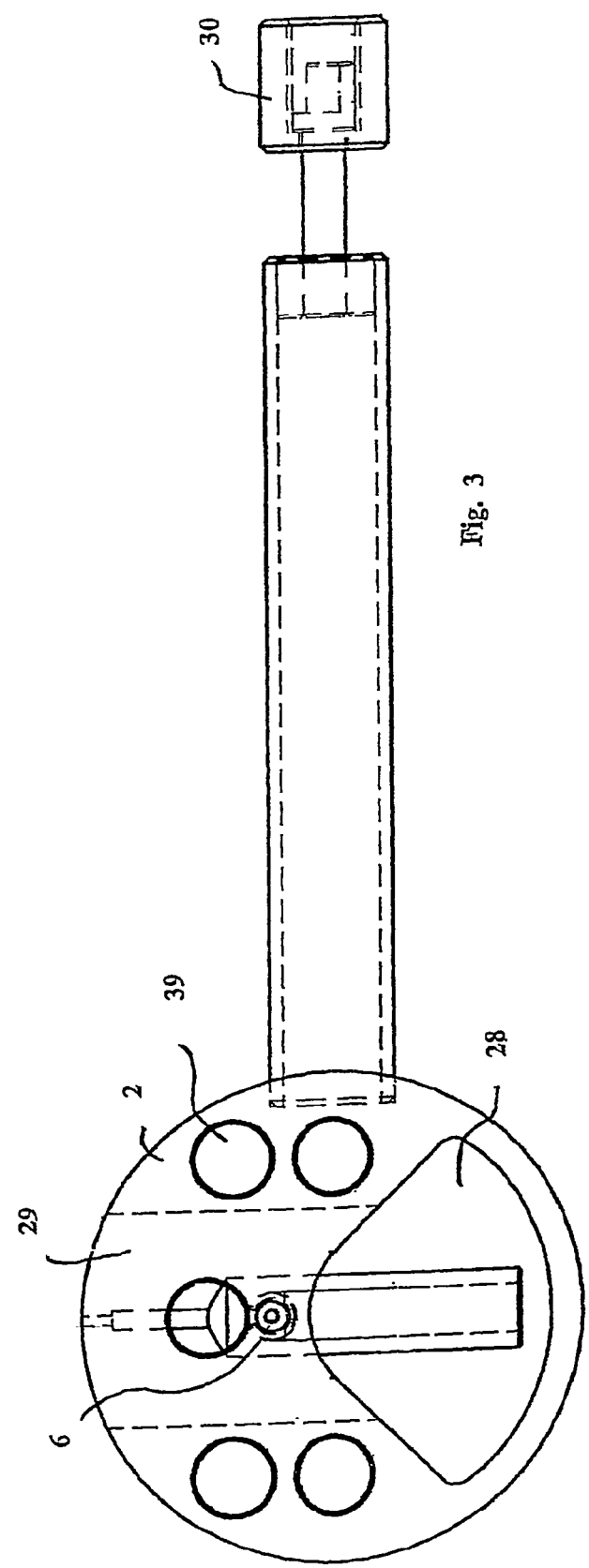

GAUGE FOR USE IN A SURGICAL PROCEDURE

FIELD OF THE INVENTION

The present invention relates to surgical implements and surgical methods and in particular to a gauge for use in surgical procedures, for example surgery involving prosthetic components.

The invention has been developed primarily for use in implanting prosthetic components in osteotomological surgery on either humans or animals, for example in relation to hip replacement surgery and the like. However it will be appreciated that the invention is not limited to this particular field of use.

BACKGROUND ART

Prior art prosthetic implant techniques have typically required the surgeon to align prosthetic components by eye. Use of this prior art technique in hip replacement surgery, for example, may result in misalignment of prosthetic components such as femoral stems and acetabular cups. This misalignment may lead to post operative complications such as misalignment of the leg, incorrect leg length and/or incorrect soft tissue tension. The long term effects of misaligned prosthetic components can also include accelerated wear of the components, aseptic loosening of the components and potentially early repetition of the surgery.

Some of these issues are at least partially addressed by the arrangement disclosed in co-pending patent application No. PCT/AU02/01482 (WO03/037192) the contents of which are hereby incorporated in their entirety by reference. This patent specification discloses the use of an alignment handle as shown in FIGS. 20 to 24 and FIG. 36.

This alignment handle has a gauge adapted to indicate whether a prosthetic component is in a predefined orientation. This alignment handle, whilst a significant improvement over the prior art, nevertheless exhibits certain limitations.

Any discussion of the prior art throughout the specification should in no way be considered as an admission that such prior art is widely known or forms part of common general knowledge in the field.

SUMMARY OF THE INVENTION

According to a first aspect of the invention there is provided a gauge for use in a surgical procedure to determine a first angle in a first plane and a second angle in a second plane, said gauge including:
 a body; and
 a plumb bob mounted to said body so as to hang under the influence of a local gravitational field, said plumb bob being rotatable relative to said body in both said first plane and said second plane so as to determine said first angle and said second angle respectively.

Preferably a universal joint rotatably mounts the plumb bob to the body. In a preferred embodiment the universal joint is a ball joint, however it will be. appreciated that other types of universal joints, such as an eye end joint, a singular pivot-point joint, a tie rod end joint or a rose joint, for example, may be utilised in alternative preferred embodiments.

Preferably the first plane is orthogonal to the second plane.

The plumb bob of a preferred embodiment includes a pointer and the body preferably includes markings disposed adjacent the pointer. More preferably, a first sub-set of the markings corresponds to angular increments of the first angle and a second sub-set of the markings corresponds to angular increments of the second angle.

A preferred embodiment of the invention includes a connector disposed on the body for connection of the gauge to a prosthetic component. An alternative preferred embodiment includes a connector disposed on the body for connection of the gauge to a predefined site of a patient.

A preferred embodiment is particularly suited for surgical applications such as the insertion of an acetabular cup into a reamed acetabulum during hip replacement surgery. For this application the first angle preferably corresponds to an aversion of the acetabular cup and the second angle preferably corresponds to an abduction of the acetabular cup.

According to a second aspect of the invention there is provided a gauge for use in a surgical procedure to determine a first angle in a first plane and a second angle in a second plane, said gauge including:
 a body;
 a first plumb bob mounted to said body so as to hang under the influence of a local gravitational field, said first plumb bob being rotatable relative to said body in said first plane so as to determine said first angle; and
 a second plumb bob mounted to said body so as to hang under the influence of a local gravitational field, said second plumb bob being rotatable relative to said body in said second plane so as to determine said second angle.

Preferably the first plumb bob is mounted to the body for rotation about a first axis and the second plumb bob is mounted to the body for rotation about a second axis, whereby the first axis is orthogonal to the second axis.

BRIEF DESCRIPTION OF THE DRAWINGS

A preferred embodiment will now be described, by way of example only, with reference to the accompanying drawings in which:

FIG. 2 is a plan view of the first embodiment;

FIG. 3 is a side view of the first embodiment;

DETAILED DESCRIPTION OF THE INVENTION

Figure 1:
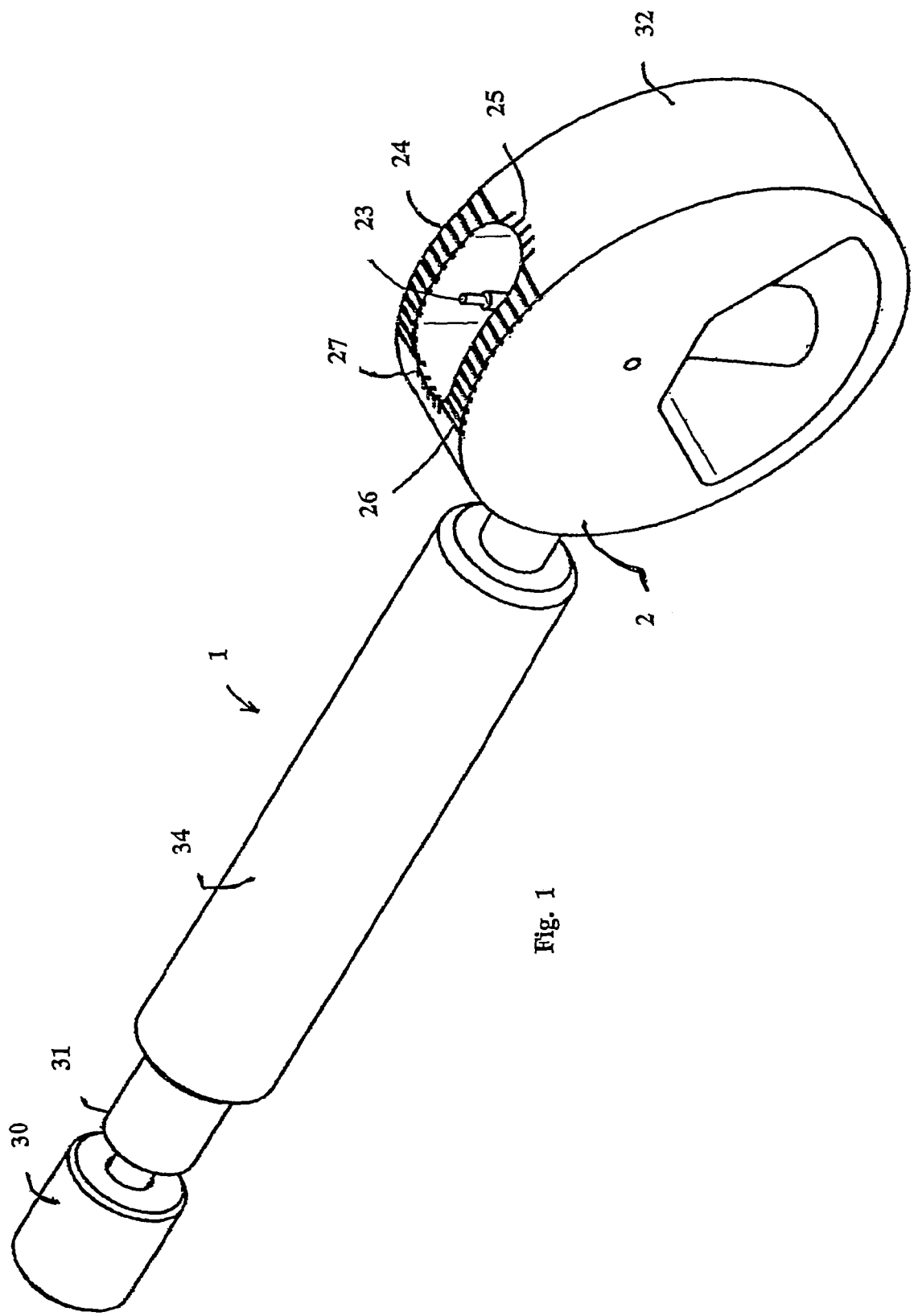
FIG. 1 is a perspective view of a first preferred embodiment of the invention.
Figure 4:
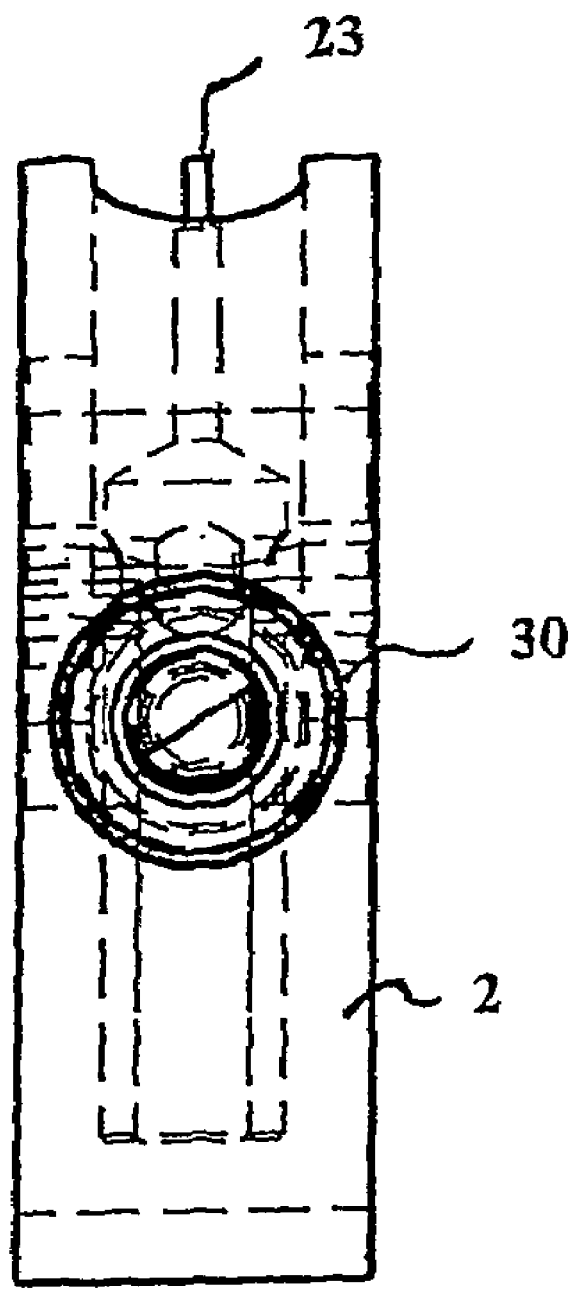
FIG. 4 is a rear view of the first embodiment.
Figure 5:
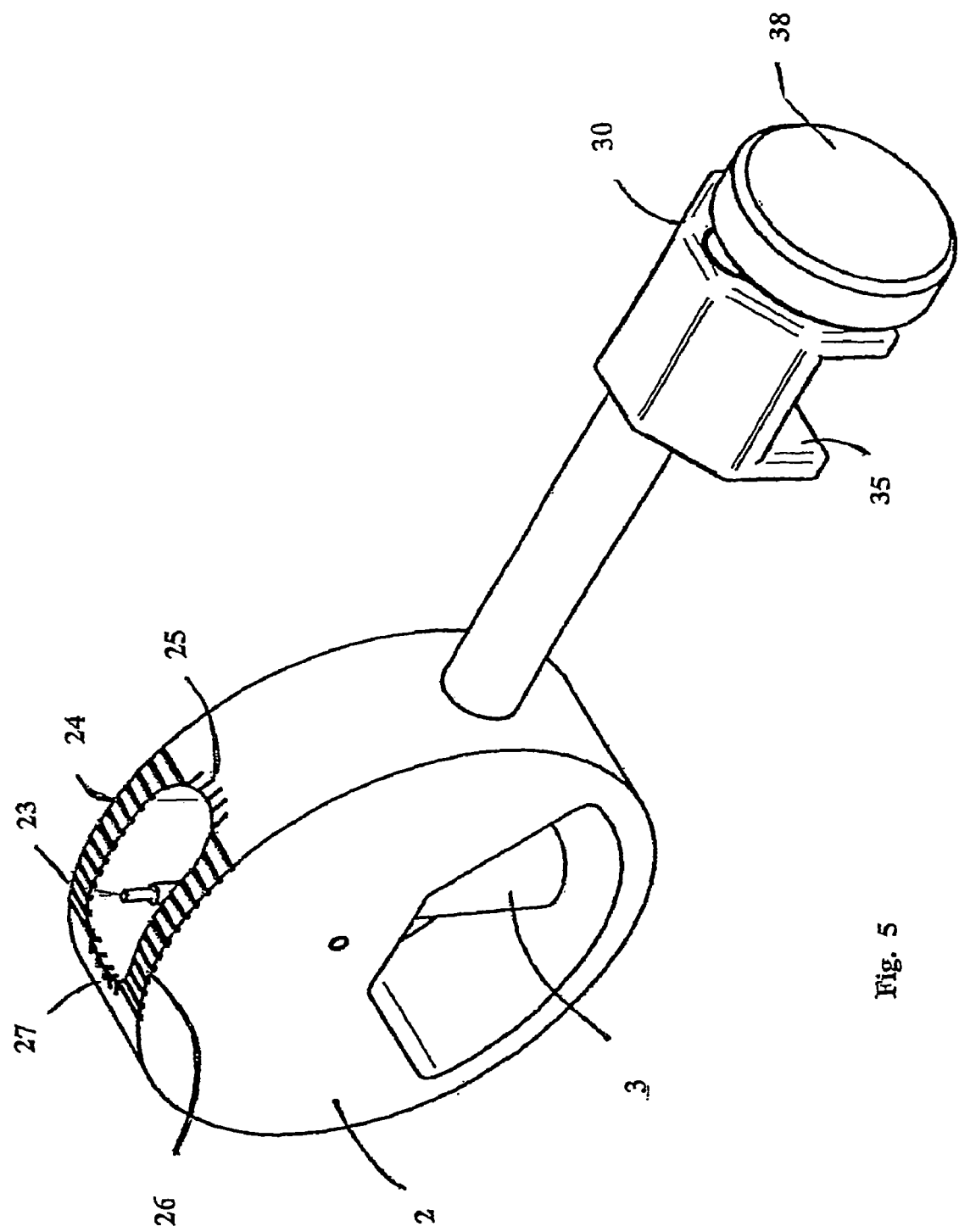
FIG. 5 is a perspective view of a second preferred embodiment of the invention.
Figure 6:
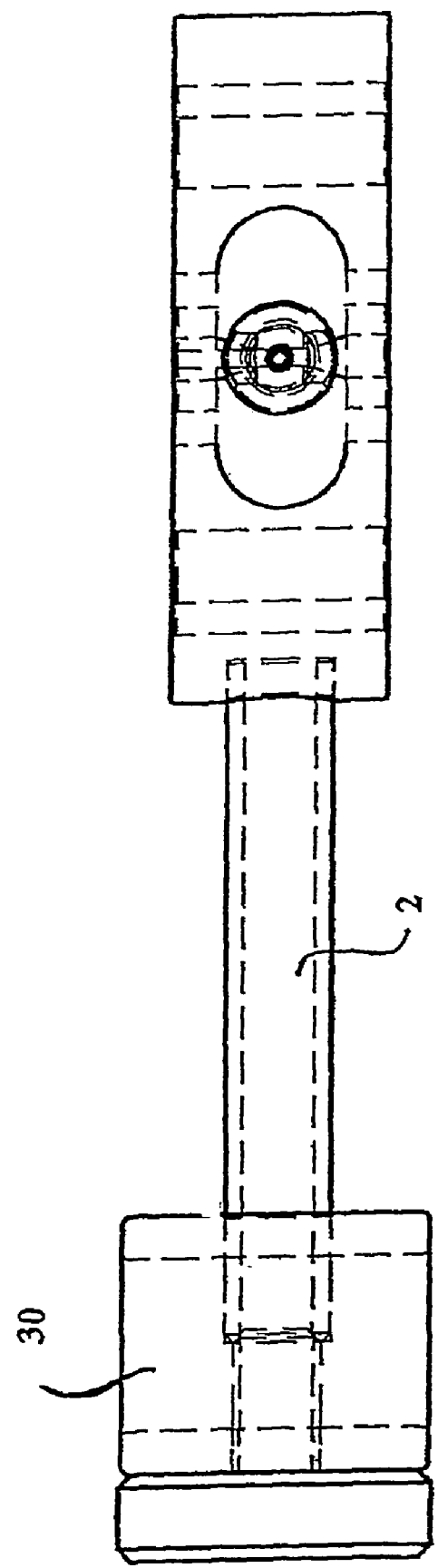
FIG. 6 is a plan view of the second embodiment.

Referring to the drawings, the first preferred embodiment of the gauge 1 includes a body 2 with a plumb bob 3 mounted to the body 2. The plumb bob 3 hangs from the body 2 under the influence of a local gravitational field. More particularly, the plumb bob 3 is rotatable relative to the body 2 in both a first plane denoted by dotted line 4 in FIG. 2 and a second plane denoted by dotted line S also shown in FIG. 2. The first plane is orthogonal to the second plane.

Figure 11:
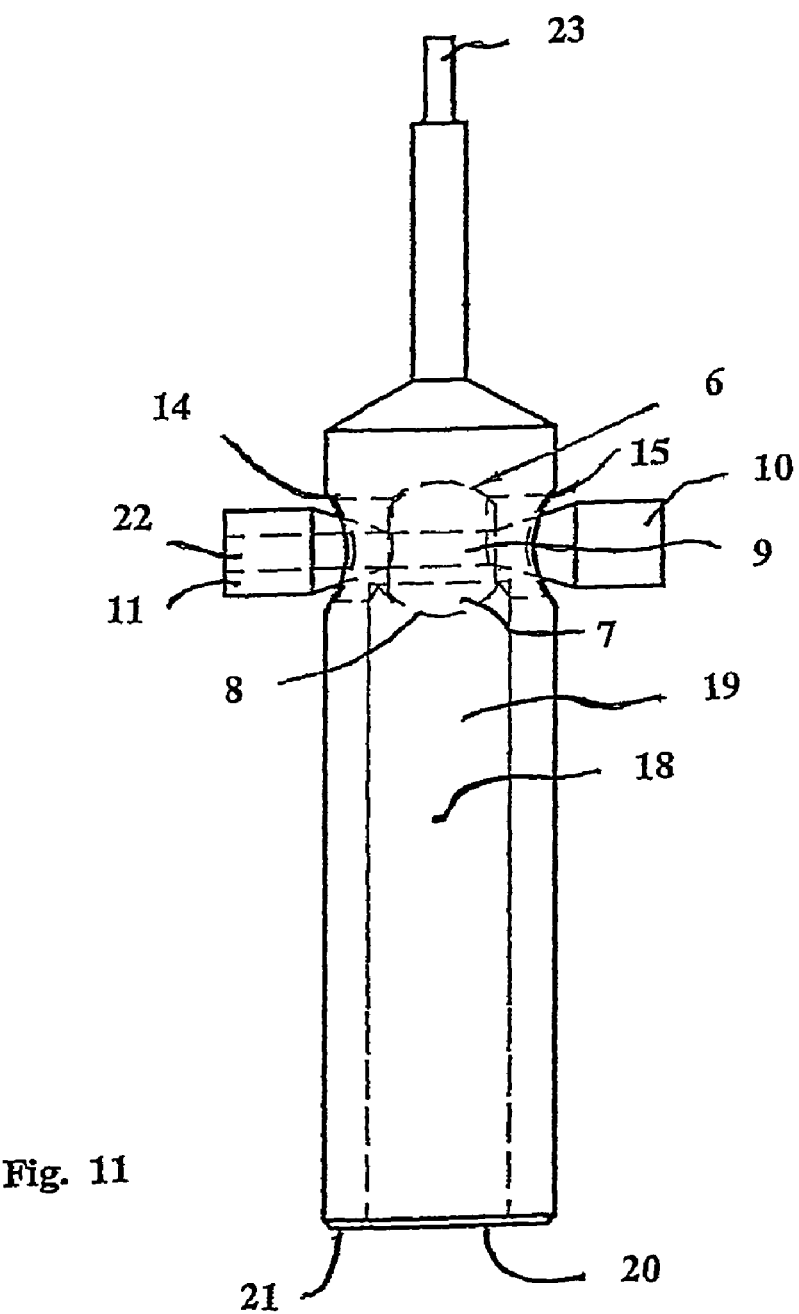
FIG. 11 is a rear view of the plumb bob shown in FIG. 9.

A universal joint, in the form of ball joint 6, rotatably mounts the plumb bob 3 to the body 2. The universal joint 6 has a ball 7 which is centrally housed within the plumb bob 3. An internal surface 8 of the plumb bob 3 has a convex shape which conforms to the concave surface of the ball 7. An axle 9 extends through the center of the ball 7 to define first and second cylindrical ends 10 and 11. Along conical sections 12 and 13 the radius of the axle 9 increases from that of the thin central part which is embedded within the ball 7 to that of the larger first and second cylindrical ends 10 and 11. The axle 9 extends through apertures 14 and 15 provided in the plumb bob. The apertures 14 and 15 define annular stops 16 and 17 respectively. The ball 7 is free to move in any direction relative to the plumb bob 3, at least until the point at which either of the conical sections 12 or 13 impacts upon the adjacent annular stop 16 or 17. The range of movement of the plumb bob 3 relative to the axle 9 is extended by the arcuate wasting of the side walls of the plumb bob 3 in the regions of the apertures 14 and 15, as best shown in FIG. 11.

To assemble the plumb bob and axle, the ball 7, plumb bob 3 and axle components are firstly fabricated separately. The plumb bob 3 is initially hollow in the region immediately below the housing for the ball 7. This allows the ball 7 to be inserted through the aperture 20 in the base 21 of the plumb bob 3. The ball 7 is then sealed inside the plumb bob 3 by core 19 which is inserted through aperture 20 and which then fills the hollow immediately below the ball 7. The thin part of the axle 9, with the first cylindrical end 10 attached, is then threaded through aperture 15 and an aperture provided in the ball 7. Finally, the second cylindrical end 11 is secured to the other side of the thin part of the axle 9 by fastener 22.

The plumb bob 3 is then mounted to the body 2 by fixedly connecting the cylindrical ends 10 and 11 to the body 2, as best shown in FIG. 2.

Figure 7:
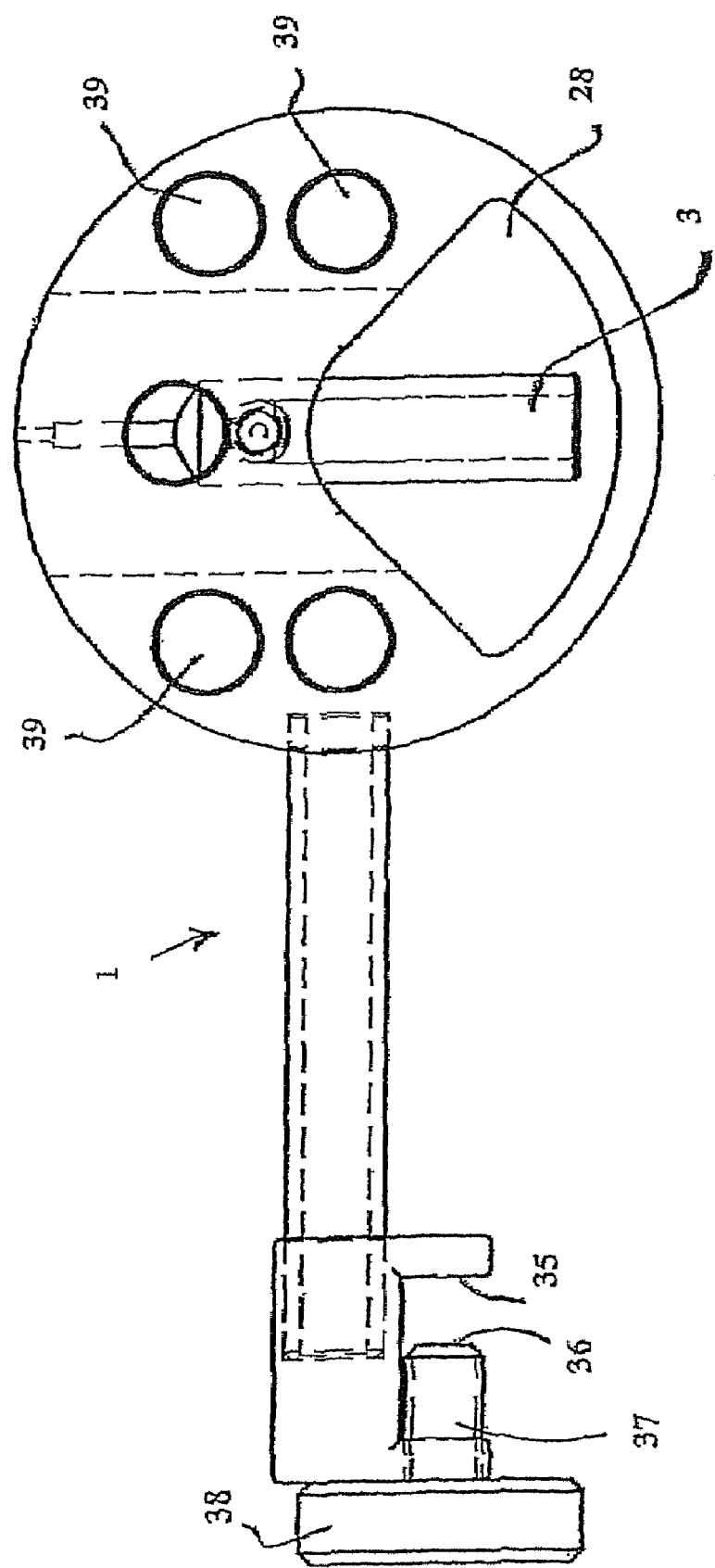
FIG. 7 is a side view of the second embodiment.
Figure 8:
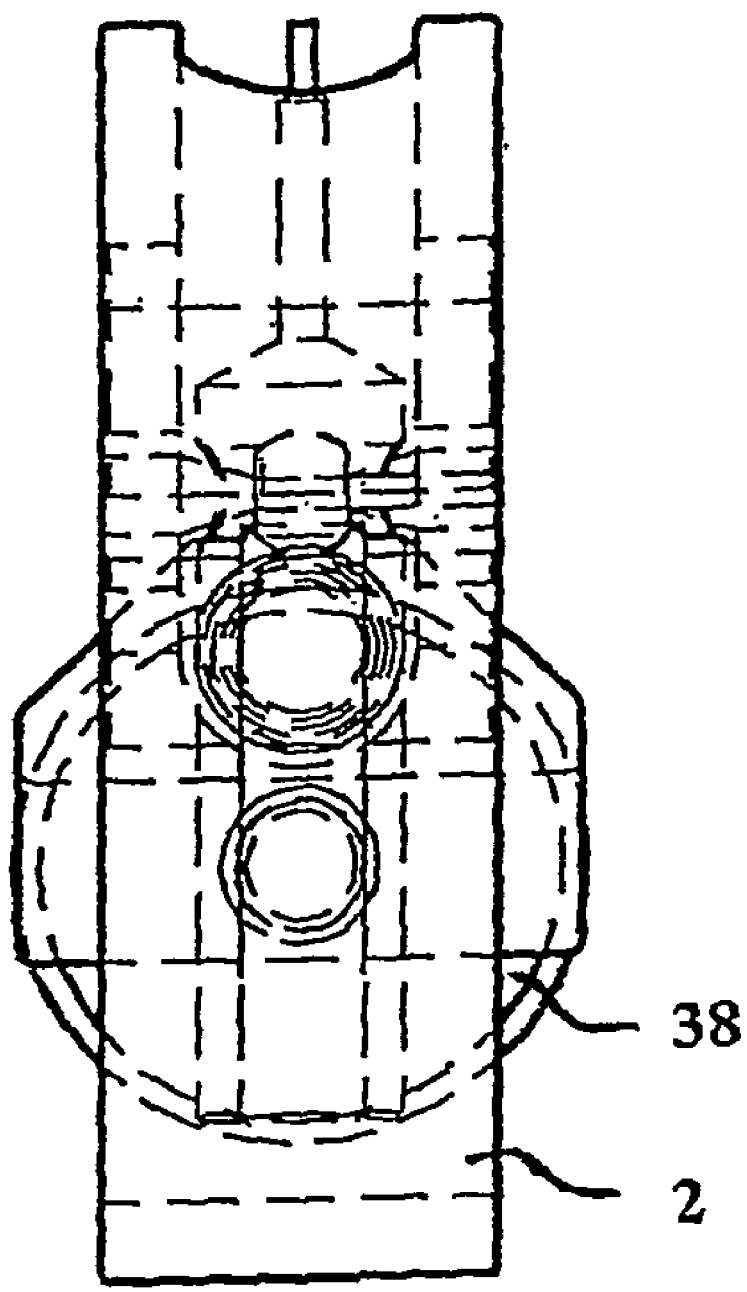
FIG. 8 is a rear view of the second embodiment.
Figure 9:
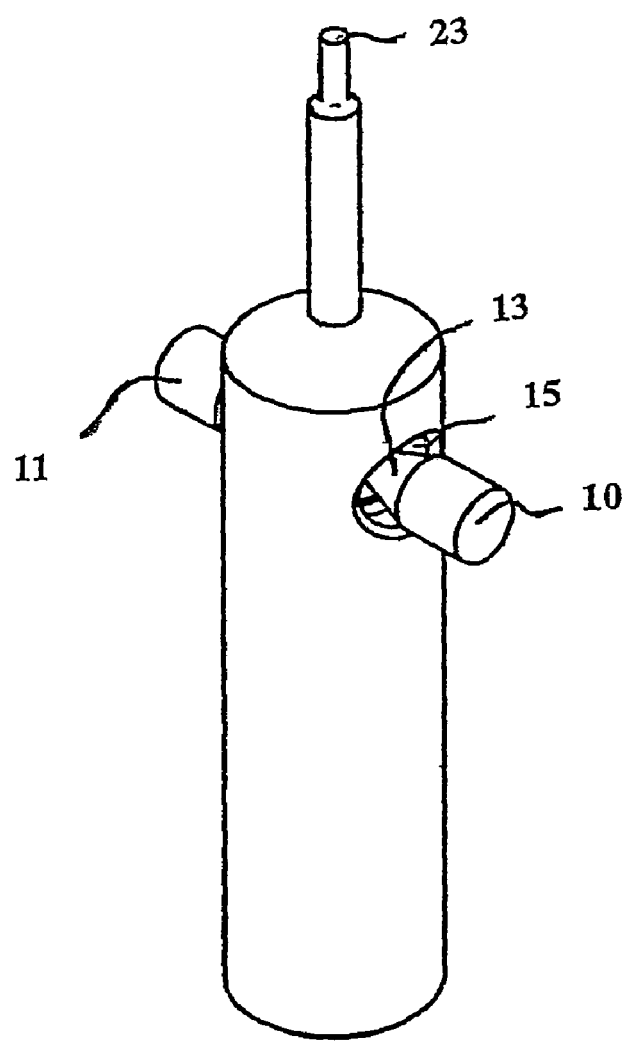
FIG. 9 is a perspective view of a plumb bob as used in both the first and second preferred embodiments of the invention.
Figure 10:
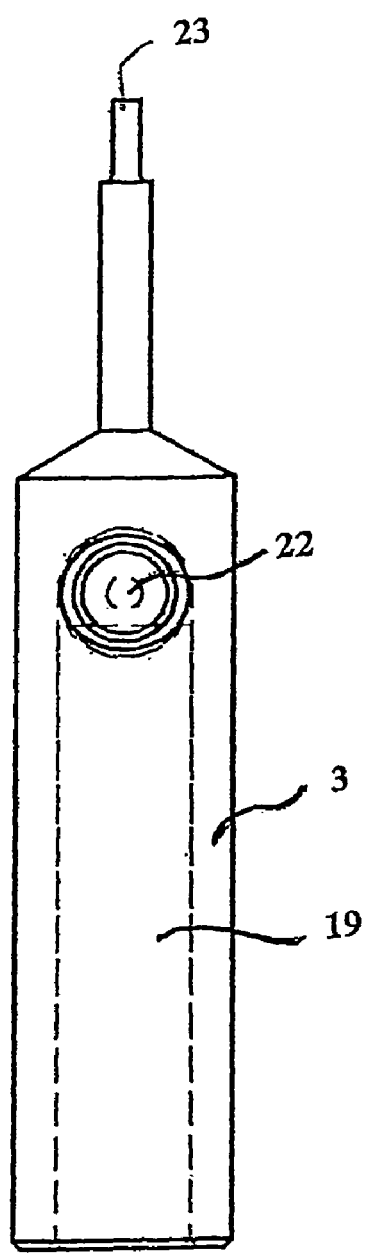
FIG. 10 is a side view of the plumb bob shown in FIG. 9.
Figure 12:
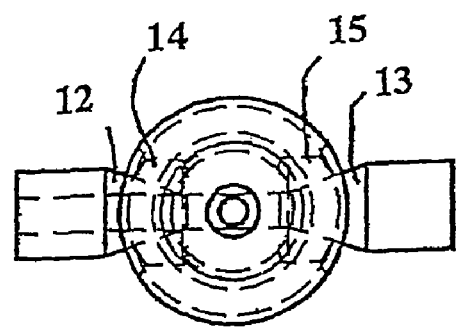
FIG. 12 is a plan view of the plumb bob shown in FIG. 9.

The body 2 includes a semi-circular opening 28 which provides clearance for the base 21 of the plumb bob 3 to assume different positions under the influence of gravity as the orientation of the gauge 1 is changed relative to a local gravitational field. To assist with weight reduction, a number of apertures 39 may be provided in the body 2, as shown for example in FIGS. 3 and 7.

In use, the body 2 is oriented relative to the plumb bob 3 such that the conical sections 12 and 13 are not in contact with the annular stops 16 and 17. This, combined with the fact that the plumb bob 3 has a center of gravity 18 which is lower than the pivot point defined by the ball 7, ensures that the plumb bob 3 is free to hang vertically due to its weight.

In alternative embodiments (not illustrated) the universal joint 6 takes other forms, for example an eye end joint, a tie rod end joint or a rose joint. The plumb bob 3 has a pointer 23 which extends above the universal joint 6. When free to hang from the ball joint 7 under the influence of gravity, the end of the pointer 23 is positioned directly above the center of the ball joint 6 and the center of gravity 18 of the plumb bob 3 is positioned directly below the center of the ball joint 6. The body 2 defines a chamber 29 which provides clearance for movement of the pointer 23.

The upper surface of the body 2 includes markings 24, 25, 26 and 27 disposed adjacent the pointer 23. A first sub-set 24 and 26 of the markings corresponds to angular increments of the first angle and a second sub-set 25 and 27 of the markings corresponds to angular increments of the second angle. In this way the gauge 1 may be used to determine a first angle in the first plane 4 and a second angle in the second plane 5. For example in one preferred embodiment, the markings 24 and 26 correspond to 5° increments of the first angle ranging from −25° at one extremity of the markings, through 0° at the center of the markings, and out to +25° at the opposite extremity of the markings. Similarly, the markings 25 and 27 correspond to 5° increments of the second angle ranging from −10° at one extremity of the markings, through 0° at the center of the markings, and out to +10° at the opposite extremity of the markings. In use, the surgeon, or other person using the preferred embodiment, can assess the position of the tip of the pointer 23 relative to markings 24 or 26 to determine the first angle. The user can also assess the position of the tip of the pointer 23 relative to markings 25 or 27 to determine the second angle. Hence, the one surgical implement advantageously allows the user to quickly and simply determine two separate angles associated with the orientation of the gauge 1 relative to a local gravitational field.

Figure 36:
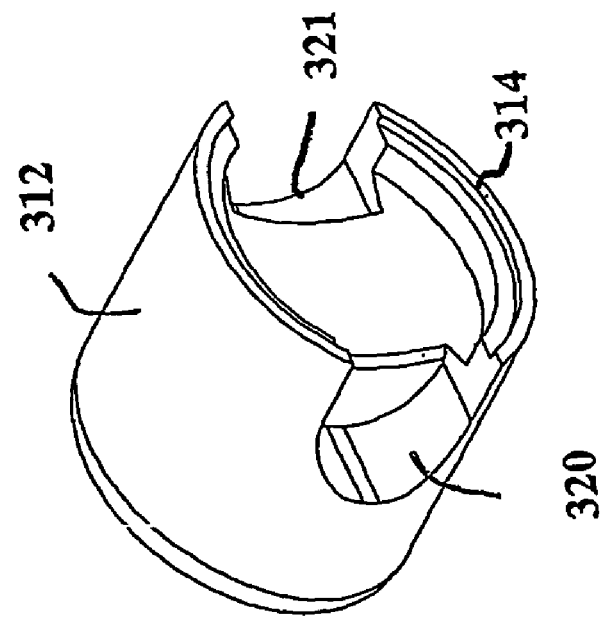
FIG. 36 is a perspective view of a lower component of a plumb bob of the fourth embodiment.
Figure 39:
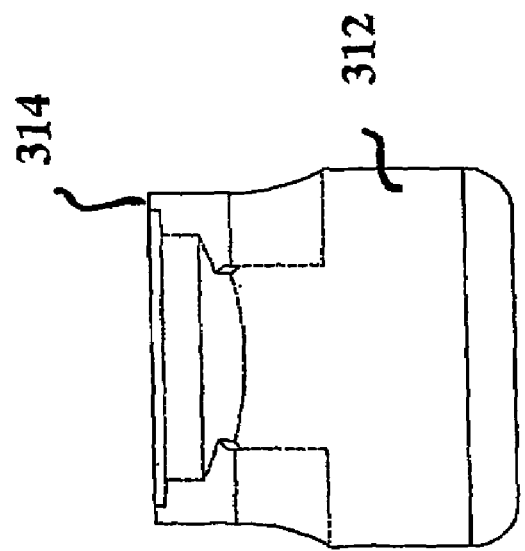
FIG. 39 is a side view of the component shown in FIG. 36.
Figure 38:
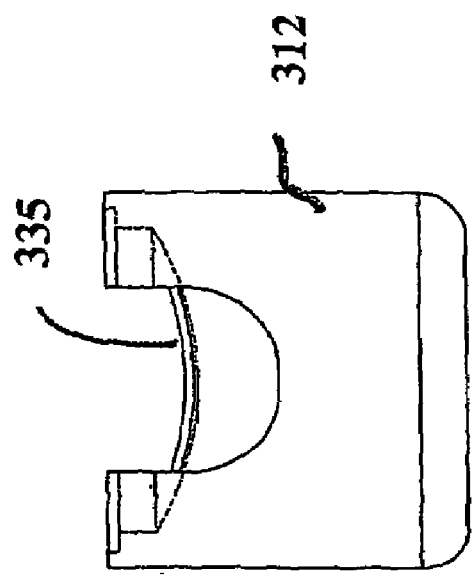
FIG. 38 is a front view of the component shown in FIG. 36.
Figure 41:
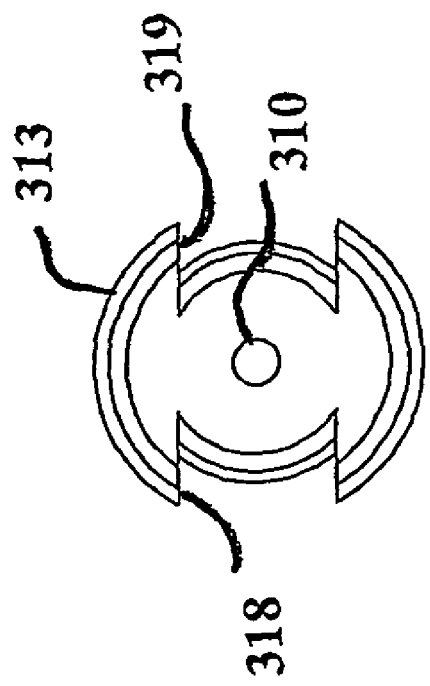
FIG. 41 is a plan view of the component shown in FIG. 40.
Figure 40:
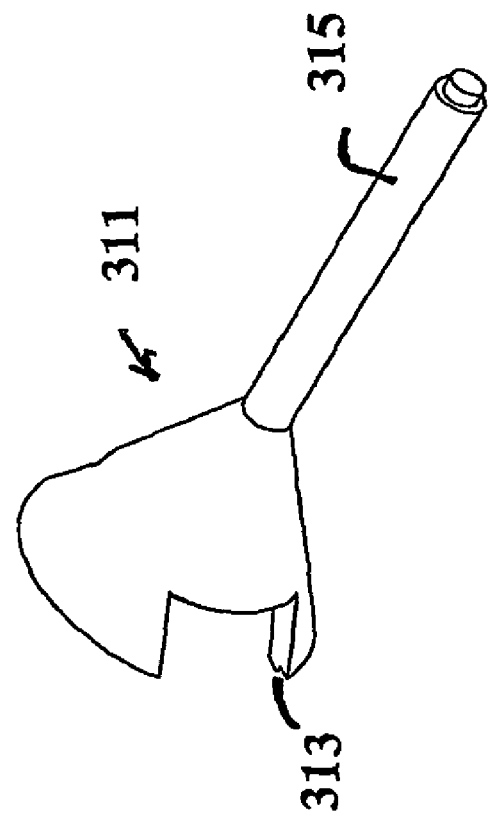
FIG. 40 is a perspective view of an upper component of a plumb bob of the fourth embodiment.
Figure 43:
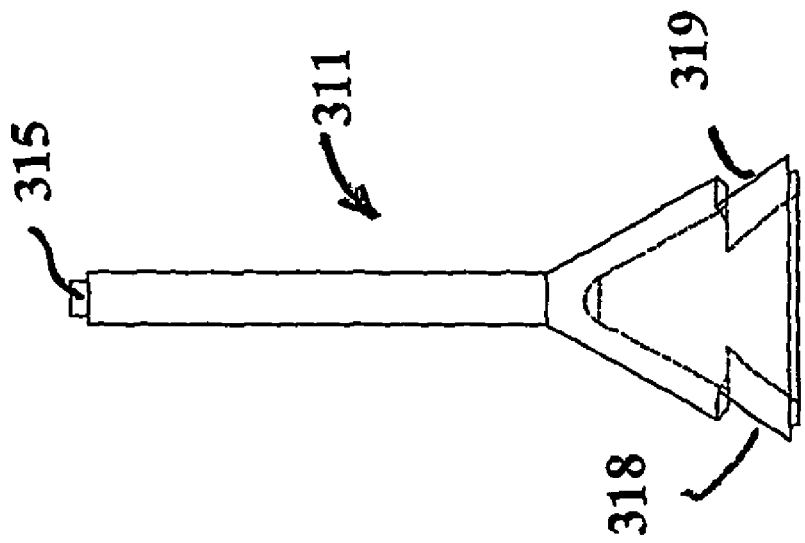
FIG. 43 is a side view of the component shown in FIG. 40.
Figure 42:
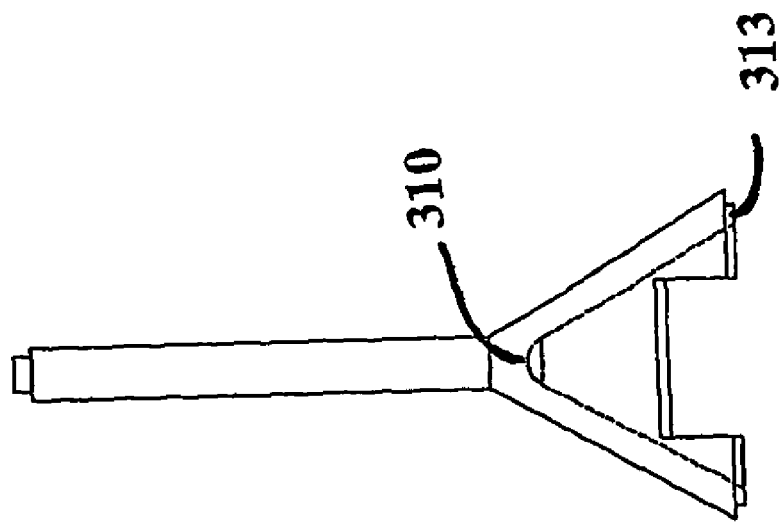
FIG. 42 is a front view of the component shown in FIG. 40.
Figure 45:
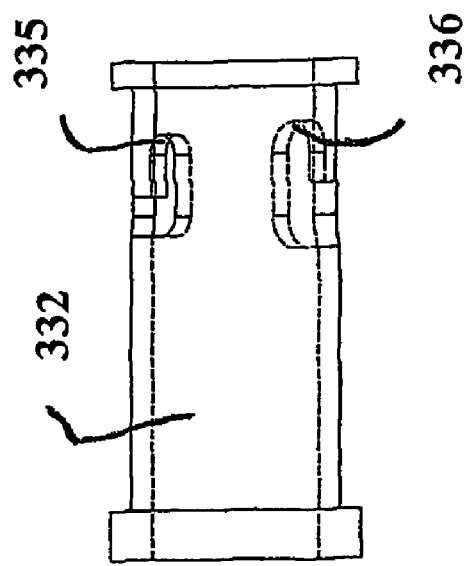
FIG. 45 is a front view of the female connector component shown in FIG. 44.
Figure 44:
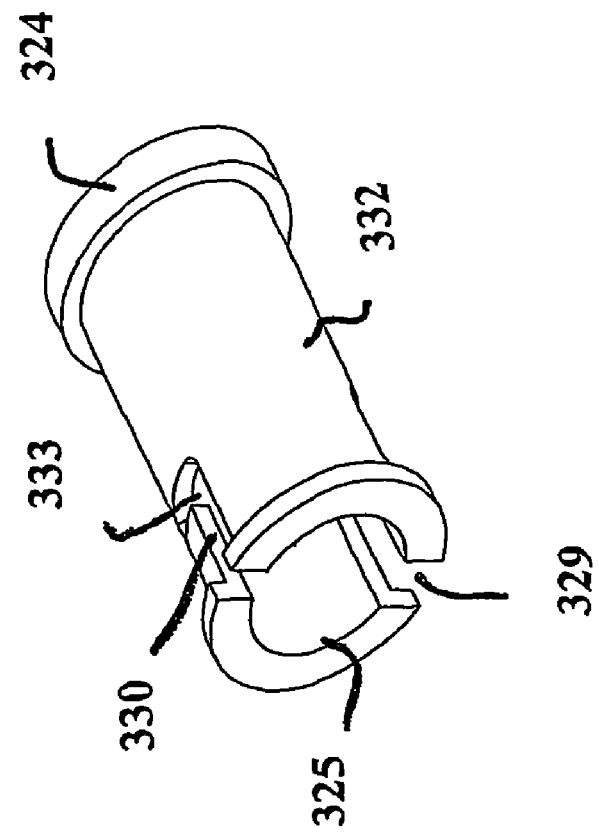
FIG. 44 is a female component of a bayonet-type connector of the fourth embodiment.
Figure 47:
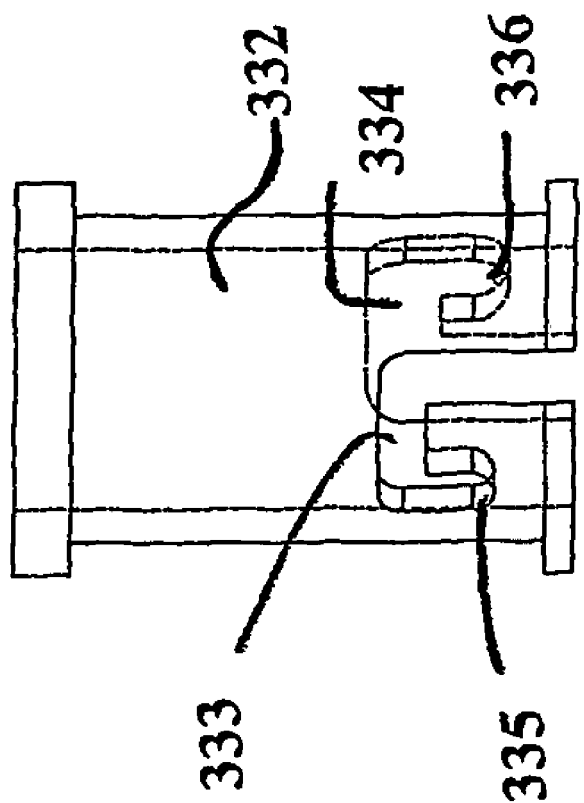
FIG. 47 is a plan view of the female connector component shown in FIG. 44.
Figure 46:
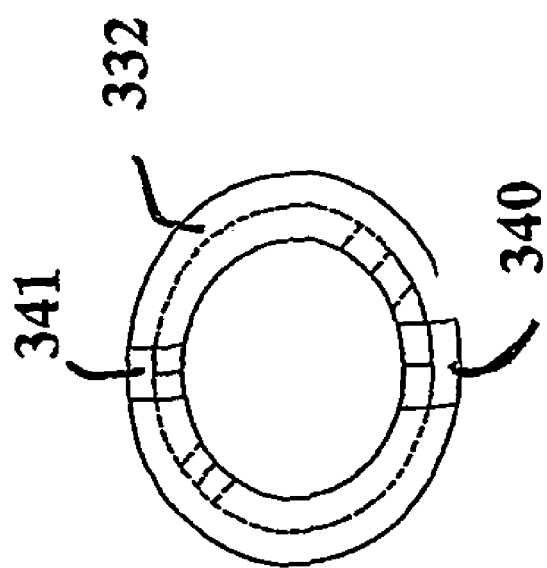
FIG. 46 is a side view of the female connector component shown in FIG. 44.
Figure 49:
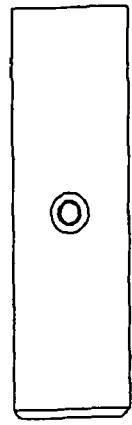
FIG. 49 is a plan view of the male connector component shown in FIG. 47.
Figure 51:
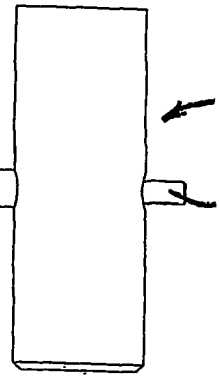
FIG. 51 is a front view of the male connector component shown in FIG. 47.
Figure 48:
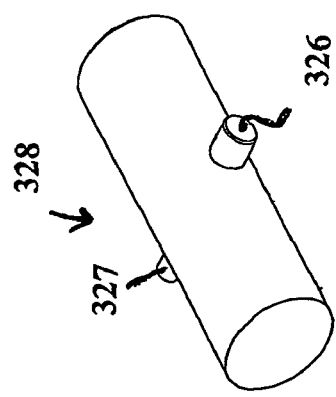
FIG. 48 is a perspective view of a male component of a bayonet-type connector for use with the gauge of the fourth embodiment.
Figure 50:
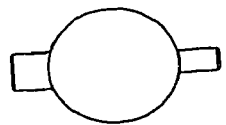
FIG. 50 is a side view of the male connector component shown in FIG. 47.

The gauge 1 of the present invention is preferably replaces the alignment handle 158 shown in FIG. 36 of co-pending PCT Application No. PCT/AU02/01482 (WO03/037192).

Figure 13:
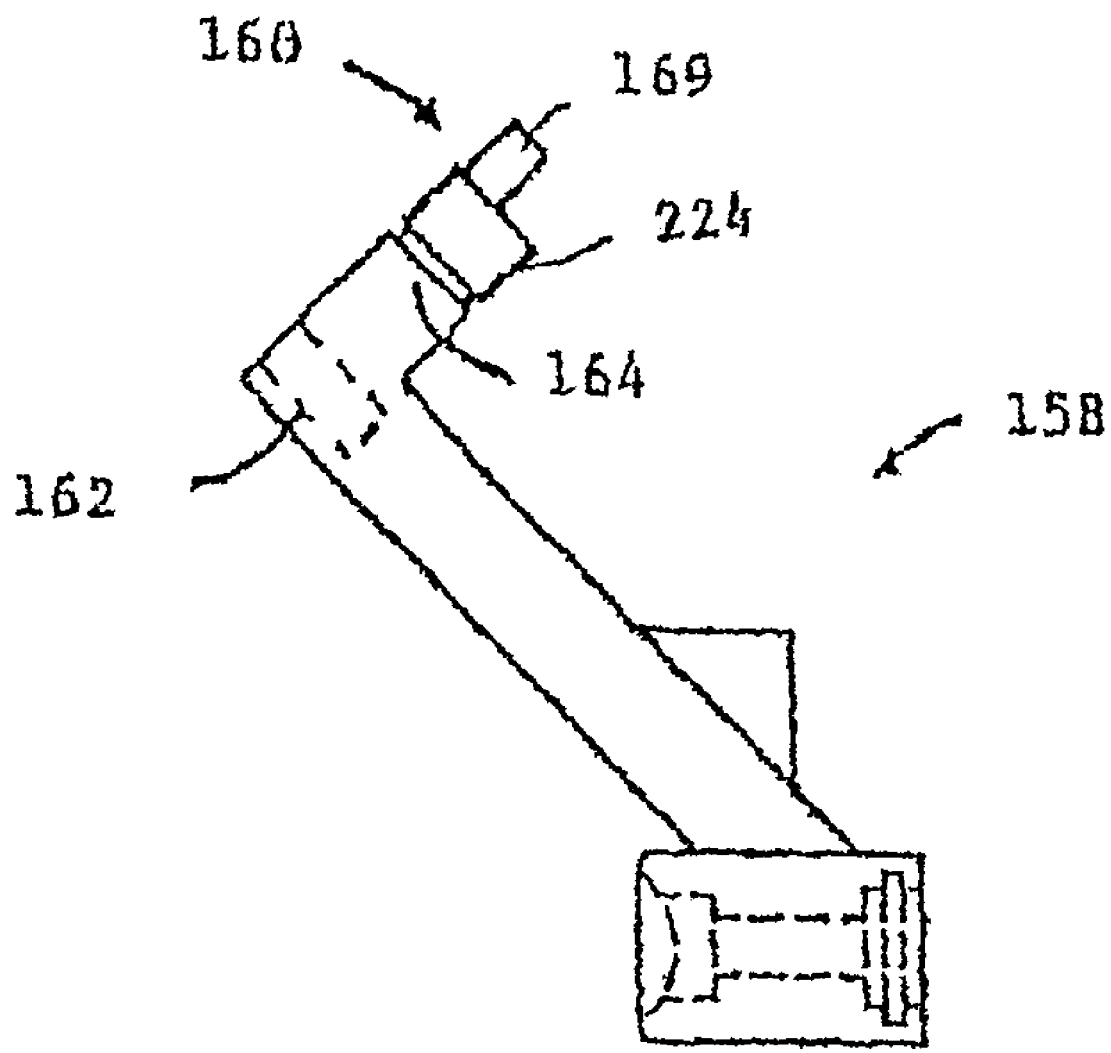
FIGS. 13 and 14 are plan views of respective left and right cup holders.
Figure 14:
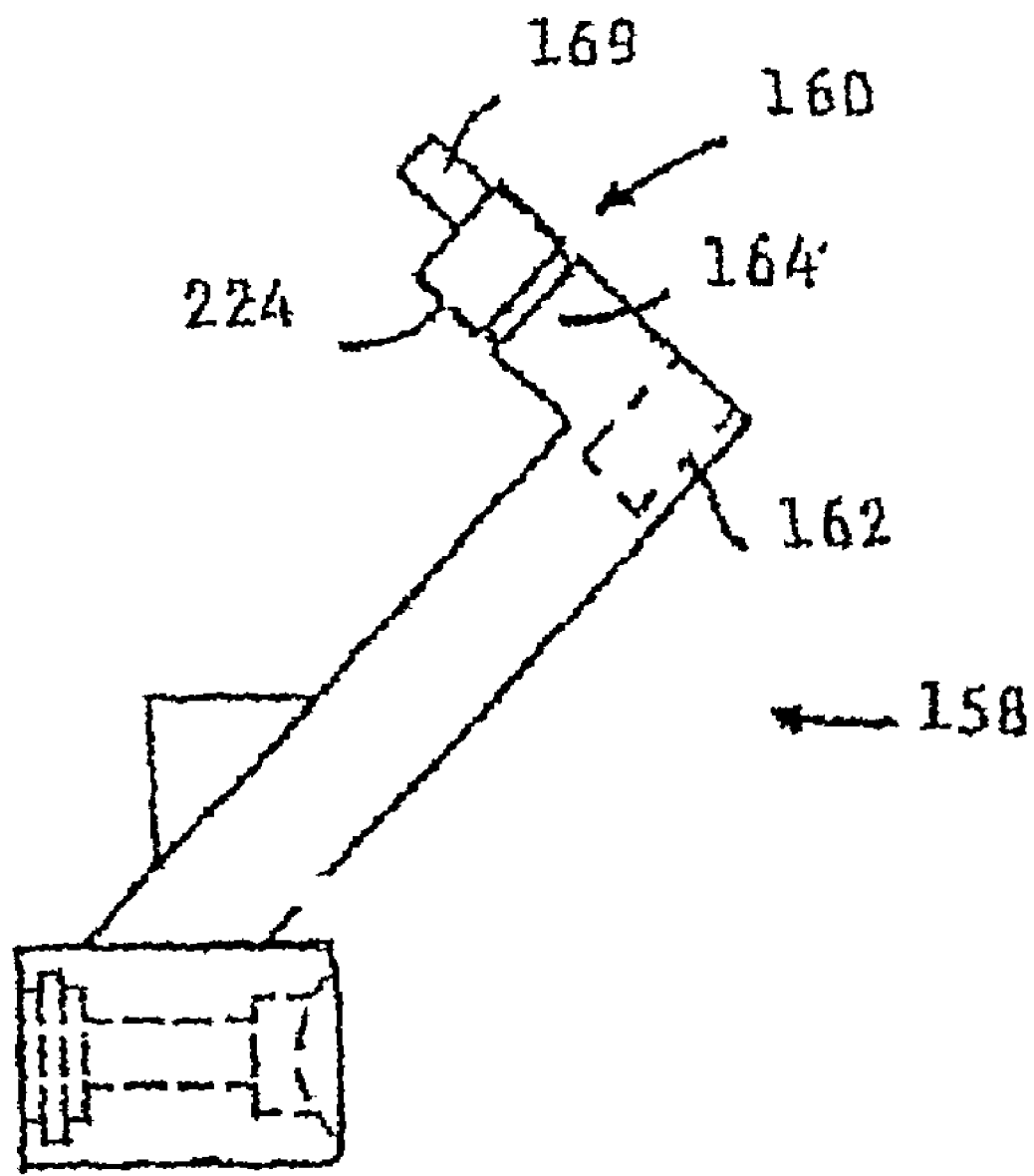

A connector 30 is disposed on the body 2 for connection of the gauge 1 to a prosthetic component, or to another surgical implement, or to a predefined site of a patient. For example, the gauge 1 may form one component of a surgical implement, for example a cup alignment tool which comprises:
 the gauge 1;
 either the left or right cup holder 158 as shown in FIGS. 13 and 14 respectively; and
 the handle 213 shown in FIG. 15.

The body 2 of the gauge 1 defines a distal end 31 and a proximal end 32, with a handle 34 intermediate the ends. The plumb bob 3 is disposed adjacent the proximal end 32. A connector, which includes an internally threaded collar 30, is disposed at the distal end 31. Assembly of the cup alignment tool requires mating of the collar 30 with either of the cup holders 158 shown in FIGS. 13 and 14. The appropriate cup holder 158 is attached to the gauge 1 via attachment means 160 disposed on a proximal end 164 of the cup holder 158. More particularly, the attachment means 160 includes a projection 169 which keys into the connector on the distal end 31 of the gauge 1 to ensure correct relative alignment between the two components. Once keyed into each other, the internally threaded collar 30 engages the external thread 224 on the cup holder 158 to secure the two components together.

Figure 15:
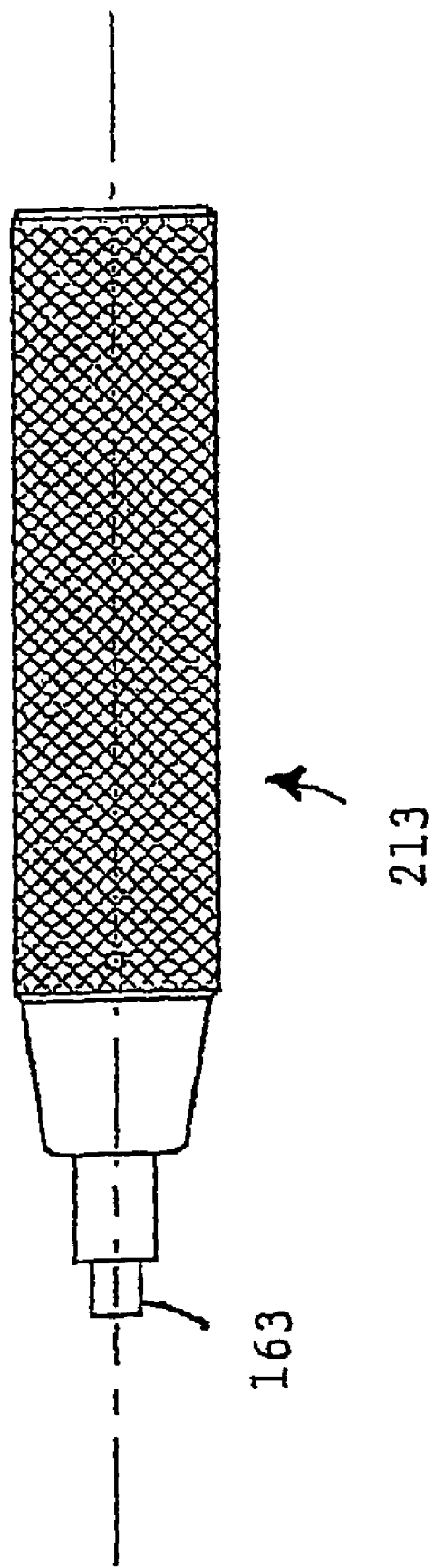
FIG. 15 is a plan view of a handle assembly.

The handle 213 show in FIG. 15 provides the surgeon with additional leverage when manipulating the cup alignment tool 167. To connect the handle 213 to the cup holder 158, an external thread 163 on the handle 213 threadedly engages an internal thread 162 disposed within the cup holder 158. The resulting cup alignment tool 167 is similar to that illustrated in FIG. 69 of co-pending PCT Application No. PCT/AU02/01482 (WO03/037192), although with the alignment handle 159 replaced by the gauge 1.

The next step is to attach a prosthetic acetabular cup of appropriate size onto the cup alignment tool (with one or more spacers if required to match the size of the prosthetic acetabular cup). The surgeon then manipulates the cup alignment tool into the wound such that the cup is adjacent the reamed acetabulum.

Figure 16:
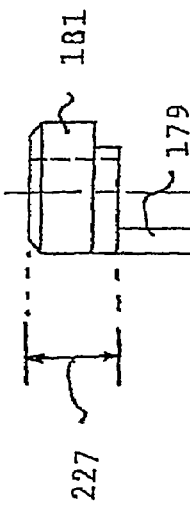
FIGS. 16 and 17 are side and plan views respectively of an alignment frame.
Figure 17:
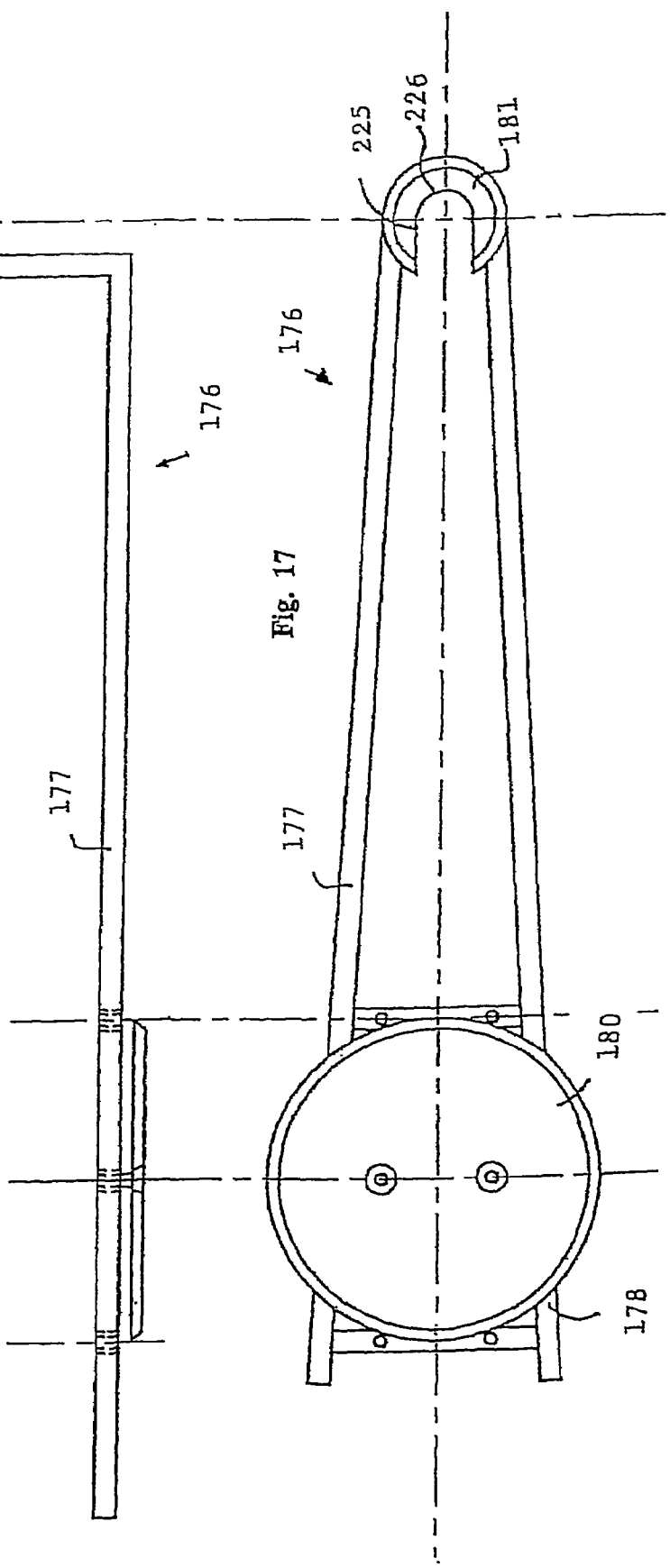
Figure 18:
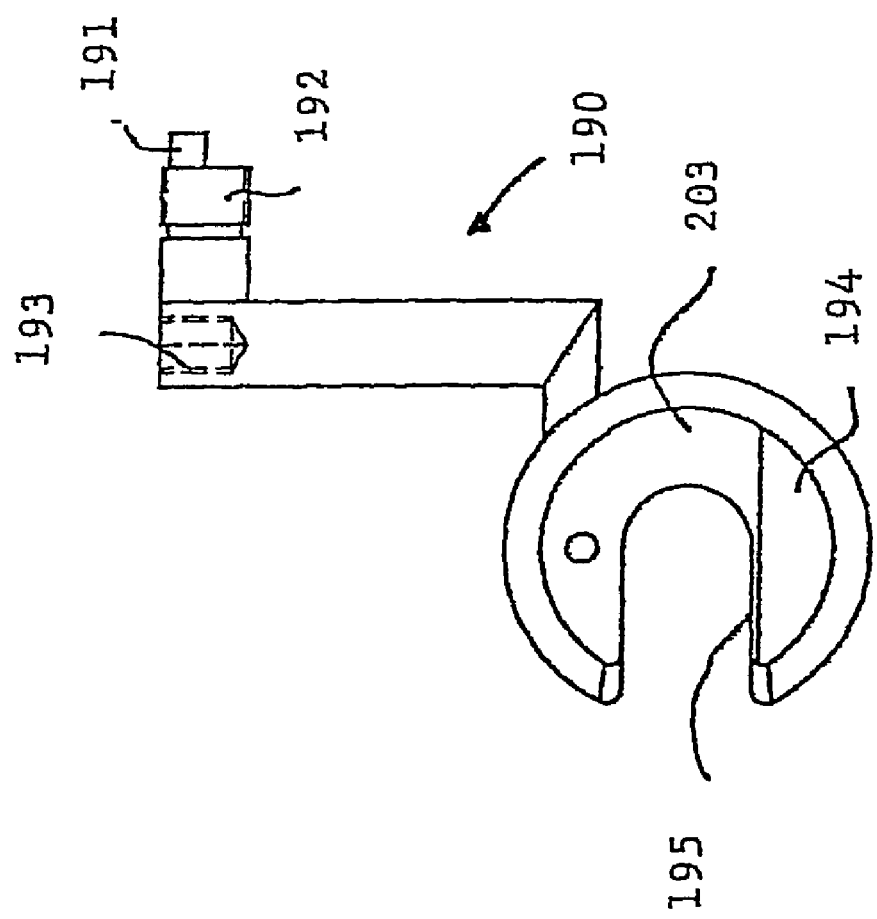
FIGS. 18 and 19 are plan views of spacer members for operating on a left and right hip respectively.
Figure 19:
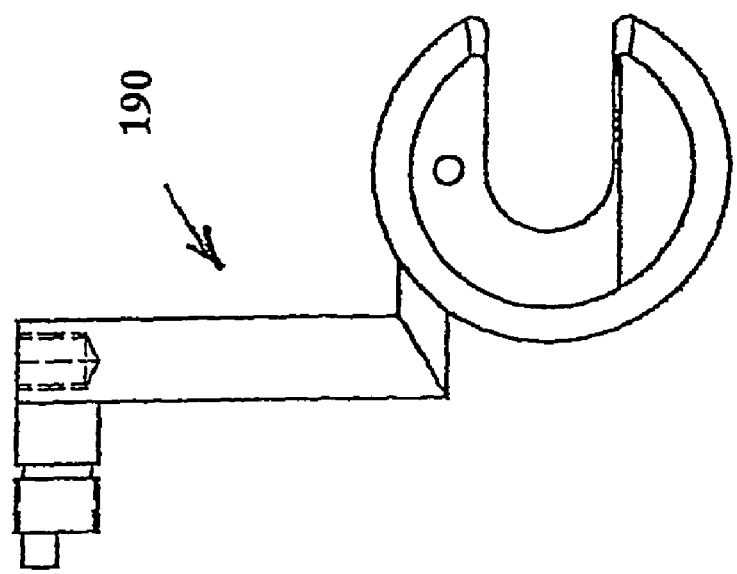

It is now necessary to orient the cup alignment tool to ensure that the prosthetic acetabular cup is in an anatomically correct orientation for insertion into the reamed acetabulum. This is achieved with reference to the two angles indicated by the pointer 23 on the gauge 1 in combination with an alignment frame 176 as shown in FIGS. 16 and 17. In other words, the cup alignment tool may be utilised by the surgeon in a manner similar to that described in co-pending PCT Application No. PCT/AU02/01482 (WO03/037192), however with the added benefit of the extra information provided to the surgeon by monitoring two angles in two different planes with the present gauge 1 rather than a single angle in a single plane as indicated by the plumb bob 173 of the alignment handle 159 disclosed in co-pending PCT Application No. PCT/AU02/01482 (WO03/037192). The geometry of the connector 158 relative to the gauge 1 and the orientation of the patient (which is maintained in a stable condition using the pelvic holder 230 shown in FIG. 20) is such that the first angle in the first plane read with reference to markings 24 or 26 corresponds to an aversion of the acetabular cup relative to the reamed acetabulum. Similarly, the second angle in the second plane read with reference to markings 25 or 27 corresponds to an abduction of the acetabular cup relative to the reamed acetabulum.

The alignment frame 176 shown in FIGS. 16 and 17 may be used to accurately align the acetabular cup in a plane other than those indicated by the plumb bob 3. The alignment flame 176 includes a frame member 177 which defines a first end 178 and a second end 179. The frame member 177 is generally 'L' shaped when viewed from the side, and 'A' shaped when viewed in plan. An abutment pad 180 is disposed on the first end 178 and is adapted to abut a planar surface, in particular the vertical side of the operating table. For example, the surgeon may use his or her knee to press the abutment pad 180 against the side of the operating table. The second end 179 of the alignment frame 176 is positioned adjacent the patient's hip.

Engagement means in the form of a slotted member 181 is disposed on the second end 179 and is aligned so as to project toward the patient's hip. The open-ended slot 225 in the slotted member 181 defines a semi circular surface 226 having an internal radius of curvature which matches an external radius of curvature of the handle 34 of the gauge 1. In other words, the slot 225 is sized so as to receive and direct the handle 34. The geometry is such that engagement of the handle 34 with the engagement means 181 forces the alignment handle 159 into a predefined orientation with respect to a third plane which is different to the two planes associated with the plumb bob 3. This is because the slotted member 181 has a width 227 sufficient to ensure that when the handle 34 is engaged with the slotted member 181, the longitudinal axis of the handle 34 matches the axis of the slotted member 181. More particularly, when the handle 34 is disposed within the slotted member 181, the handle 34, and therefore the gauge 1, is substantially perpendicular to the side of the operating table. Whilst in this position, the surgeon can tilt the gauge 1 to adjust the aversion and rotate the gauge 1 to adjust the abduction.

Figure 20:
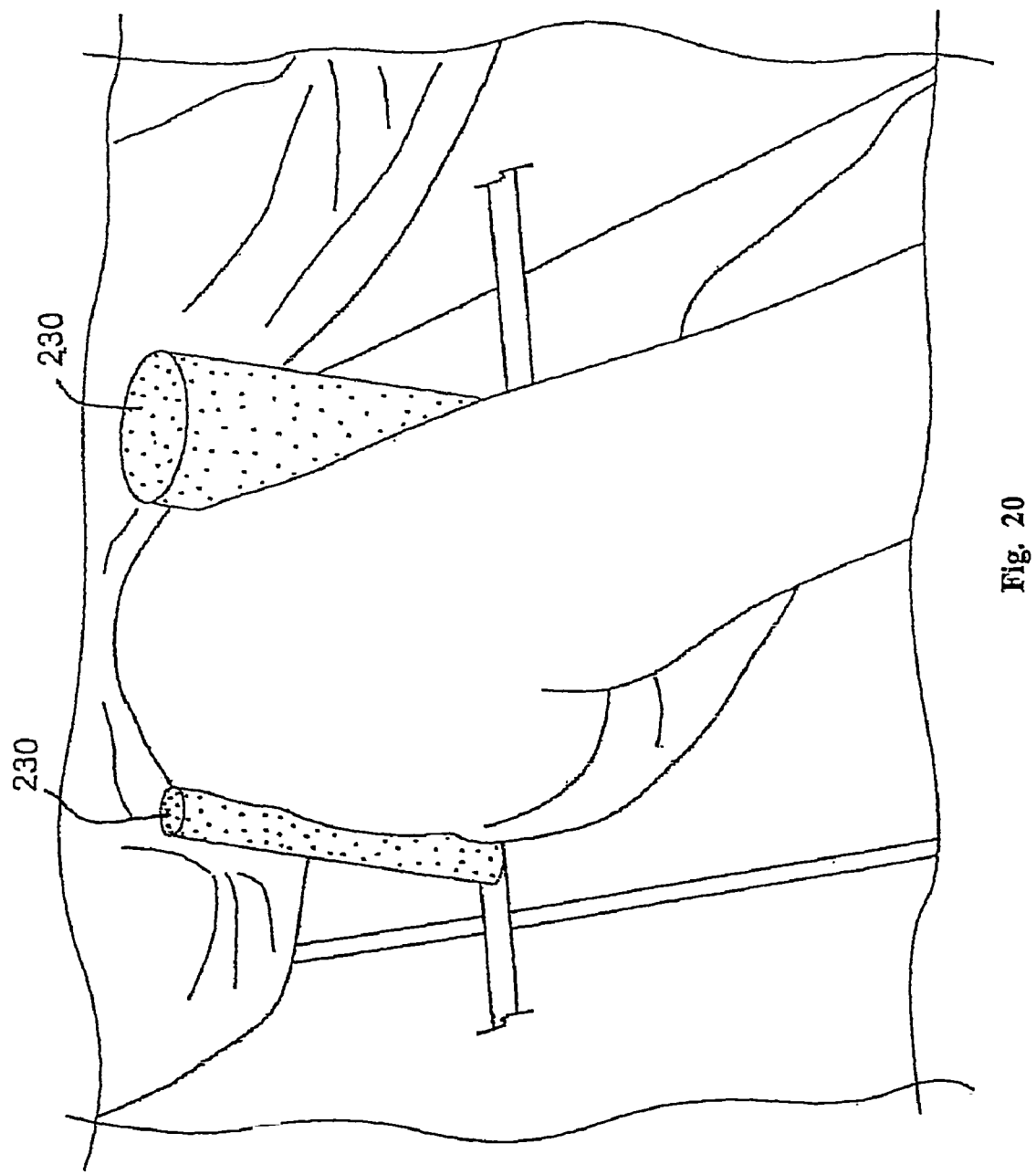
FIG. 20 is a perspective view of a patient immediately prior to commencement of hip replacement surgery.

Hence, when each of the following conditions are met:
 the patient's hip is in the predefined position on the operating table as shown in FIG. 20;
 the first end 178 of the alignment frame 176 is abutted against the side of the operating table adjacent the patient's hip so that the slotted member 181 faces the patient's hip;
 the handle 34 of the gauge 1 is engaged with the slotted member 181; and
 the pointer 23 of the gauge is indicating the desired angles for the aversion and the abduction, then the surgeon can be confident that the prosthetic acetabular cup is correctly positioned for insertion into the patient's hip. At this point the surgeon utilises a punch assembly to impact the acetabular cup into the reamed acetabulum.

Figure 21:
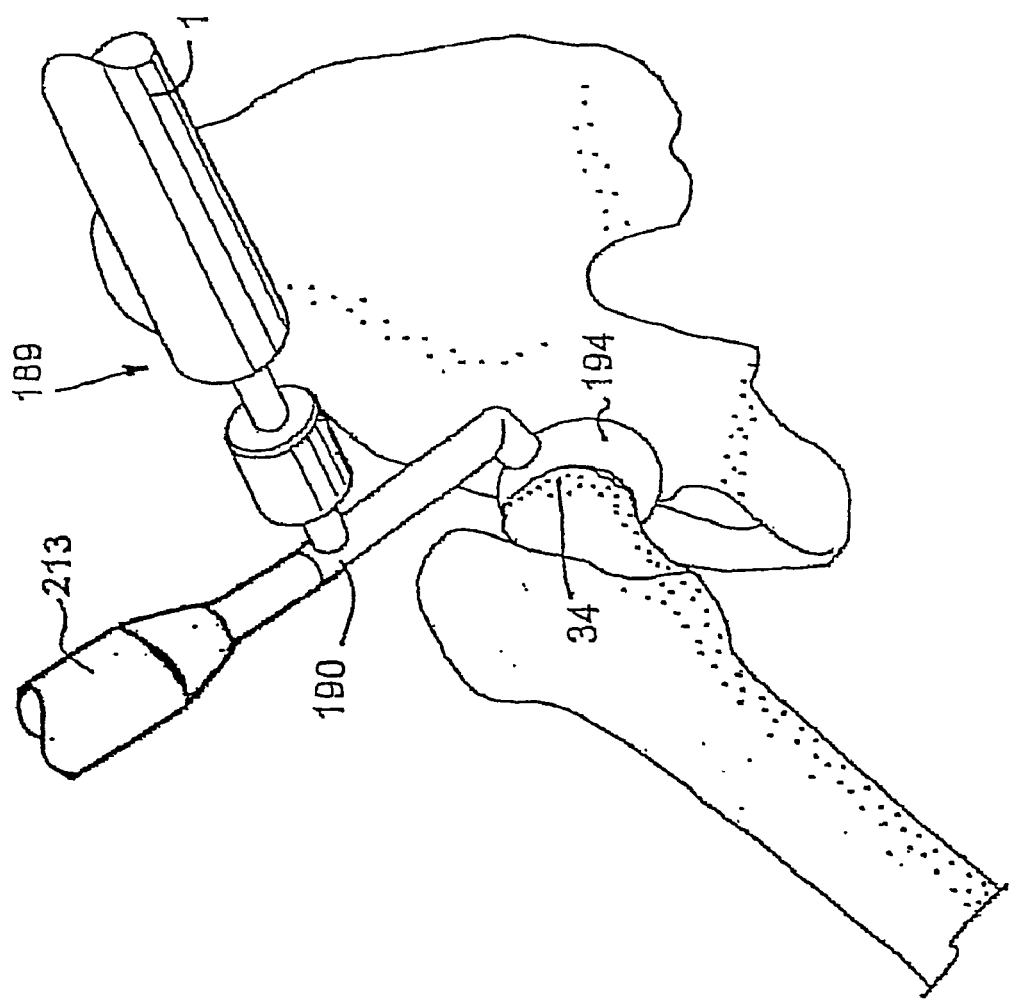
FIG. 21 is a perspective view showing part of a spacer alignment tool being applied to a patient's acetabulum.

Another step in a typical hip replacement operation is insertion of a stem into the femoral canal. After insertion, an end 34 of the stem 33 projects from the end of the femur. It is now necessary to determine the prosthetic neck length required for post operative correct leg length, tissue tension and muscle tension. A short trial head is placed onto the stem and the hip joint is reduced. As best shown in FIG. 21, a spacer alignment tool 189 is assembled by connecting a left or right spacer member 190, as required, to the gauge 1 in a similar manner to the way in which the cup holder 158 was previously attached to the gauge 1. That is, the projection 191 keys into an aperture disposed in the connector 30 on the distal end 31 of the gauge 1. The collar 30 threadedly engages the proximal end 192 of the spacer member 190. Also similar to the previous assembly of the cup alignment tool, the handle 213 is screwed into the spacer member 190 at internal thread 193 provided adjacent the proximal end 192 of the spacer member 190. In other words, to assemble the spacer alignment tool 189, simply start with the cup alignment tool and replace the cup holder 158 with the spacer member 190.

The spacer member 190 includes a spacer 194 which has a slot 195 adapted to engage an end 34 of the prosthetic stem which has been inserted into the femoral canal. This positions the spacer 194 intermediate the trial head and the end 34 of the femur, as shown in FIG. 21 (although the trial head is obscured within the reamed acetabulum). When properly positioned, the trial head is disposed within the hemispherical surface 203. Once again the surgeon may make use of the plumb bob 3 on the gauge 1 in combination with the alignment frame 176 to ensure that the spacer 194 and the trial head are oriented in an anatomically correct manner whilst performing tests to determine an appropriate prosthetic neck length.

Another exemplary application for the gauge 1 is measurement of the natural geometry of a patient prior to insertion of prosthetic components. For example, once a hip joint has been dislocated, a surgeon may wish to measure the naturally occurring aversion and abduction angles of a patient's acetabulum. For such an application the gauge 1 is connected to a connector which is abutted against the patient's acetabulum and the gauge is maintained in a predefined relationship relative to the patient (for example by means of a pelvic holder 230 as shown in FIG. 20 and an alignment frame as shown in FIGS. 16 and 17 in a similar manner to that described above). This allows the surgeon to determine the natural aversion angle from the markings 24 or 26 and the natural abduction angle from the markings 25 or 27. These figures are then noted for subsequent use, for example the surgeon may choose to insert the prosthetic acetabulum at the same aversion and abduction angles as the natural angles determined above.

The alternative preferred embodiment of the gauge 1 shown in FIGS. 5 to 8 is substantially identical to the preferred embodiment of the gauge shown in FIGS. 1 to 4, however with the exception of the provision of a different connector 30 which is in the form of a clamp. This clamp includes a lug 35 fixedly disposed opposite an end 36 of a bolt 37. Hence, part of an object to which the gauge 1 is to be connected may be placed intermediate the lug 35 and the bolt end 36. The bolt head 38 is then rotated so as to screw the bolt end 36 toward the lug 35, thereby clamping the gauge 1 to the object.

Figure 22:
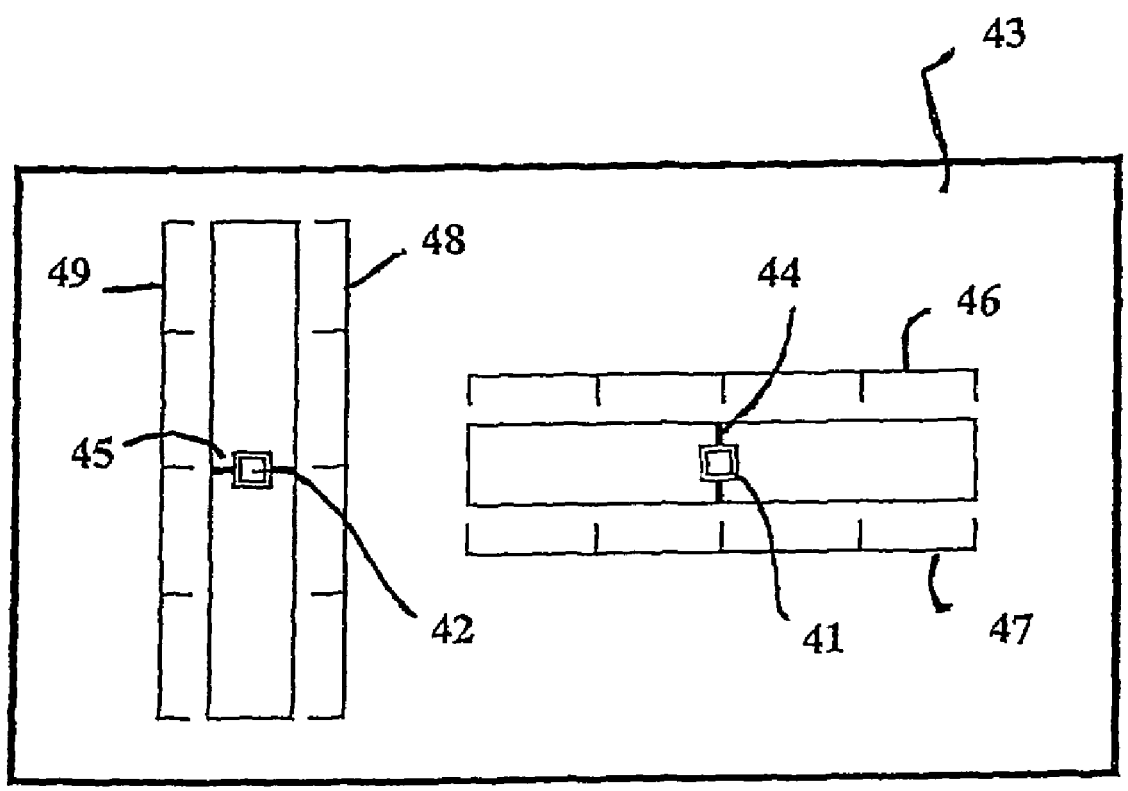
FIG. 22 is a plan view of a read-out face of a third preferred embodiment of the invention.
Figure 23:
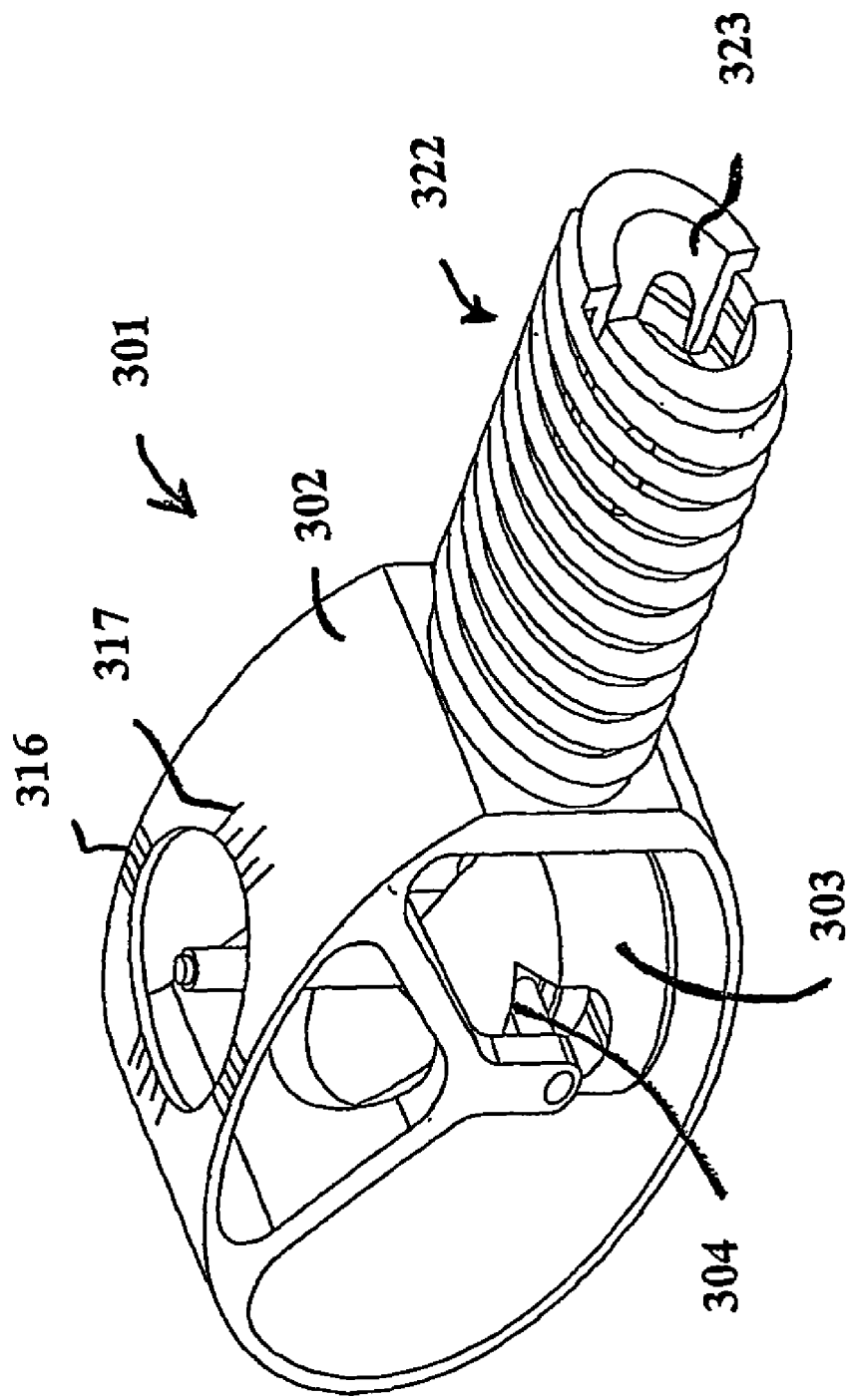
FIG. 23 is perspective view of a fourth embodiment of the invention.
Figure 24:
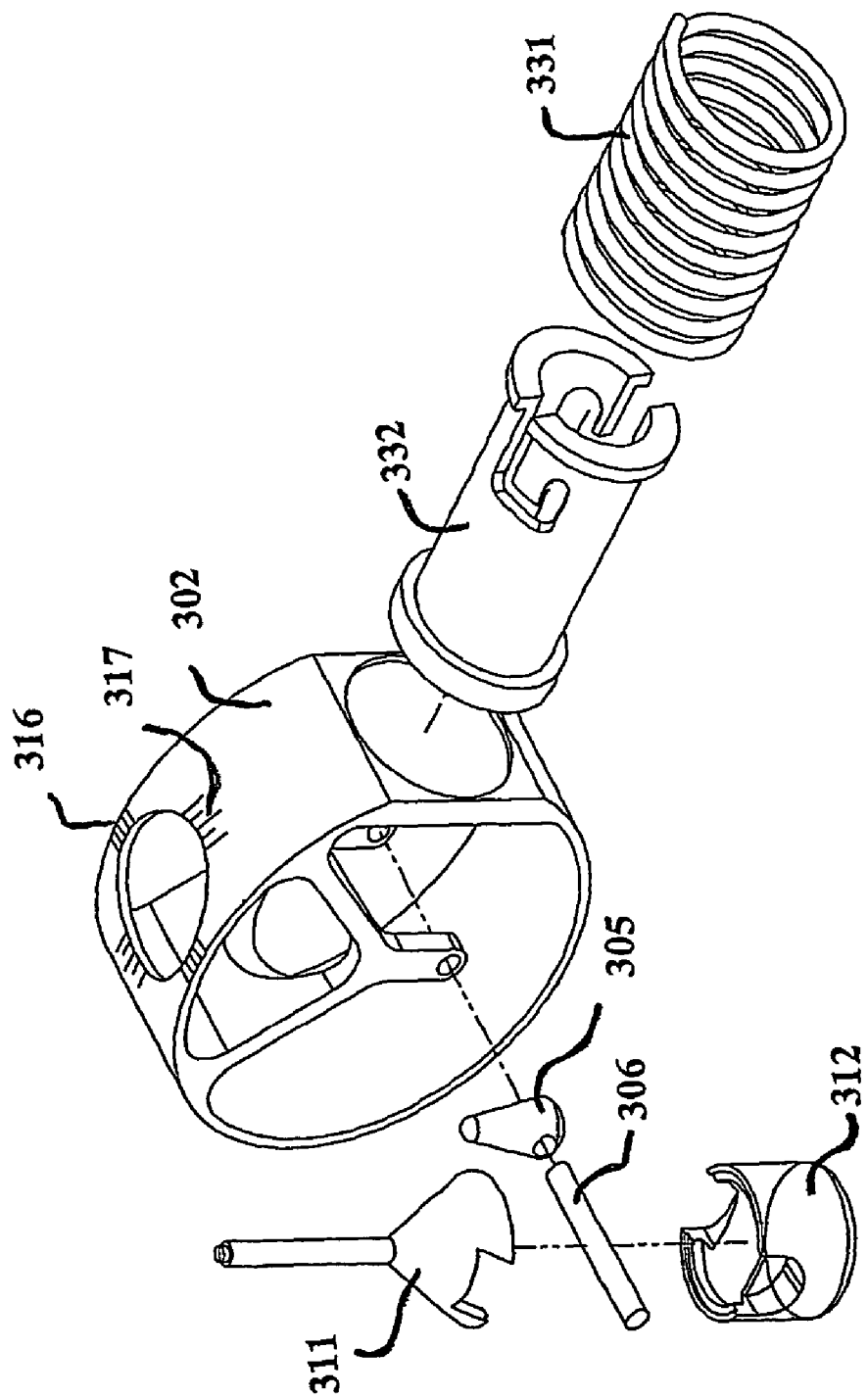
FIG. 24 a perspective disassembled view of the fourth embodiment.
Figure 26:
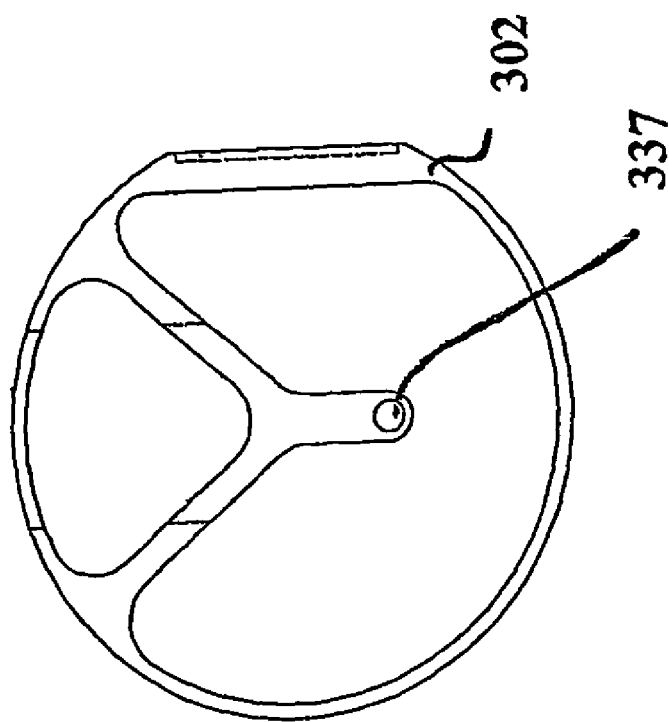
FIG. 26 is a front view of the body of the fourth embodiment.
Figure 25:
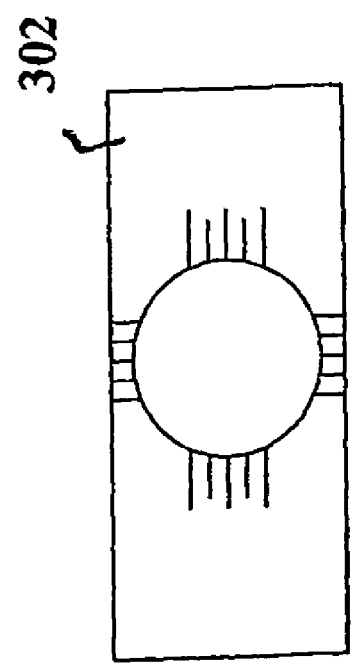
FIG. 25 is a plan view of a body of the fourth embodiment.
Figure 28:
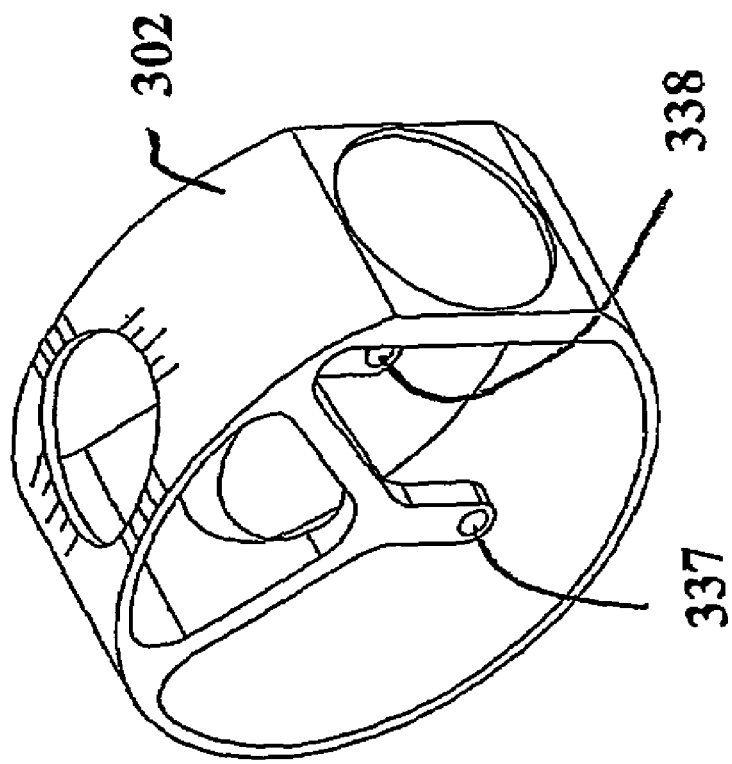
FIG. 28 is a perspective view of the body of the fourth embodiment.
Figure 27:
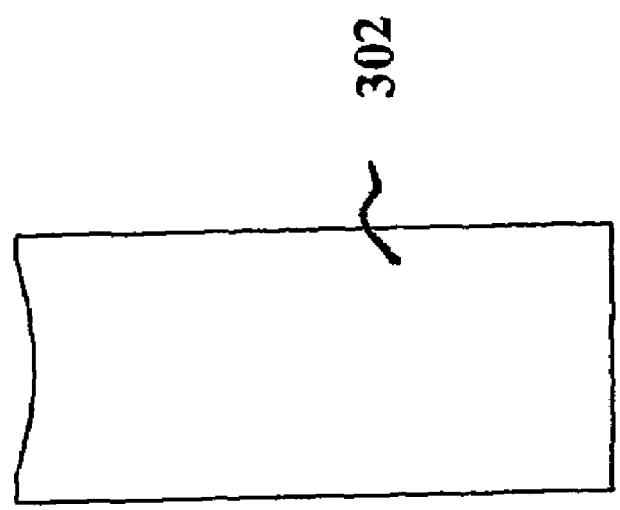
FIG. 27 is a side view of the body of the fourth embodiment.
Figure 30:
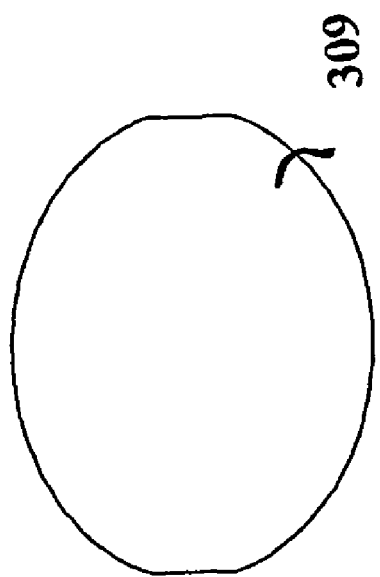
FIG. 30 is a bottom view of the pivot member of the fourth embodiment.
Figure 29:
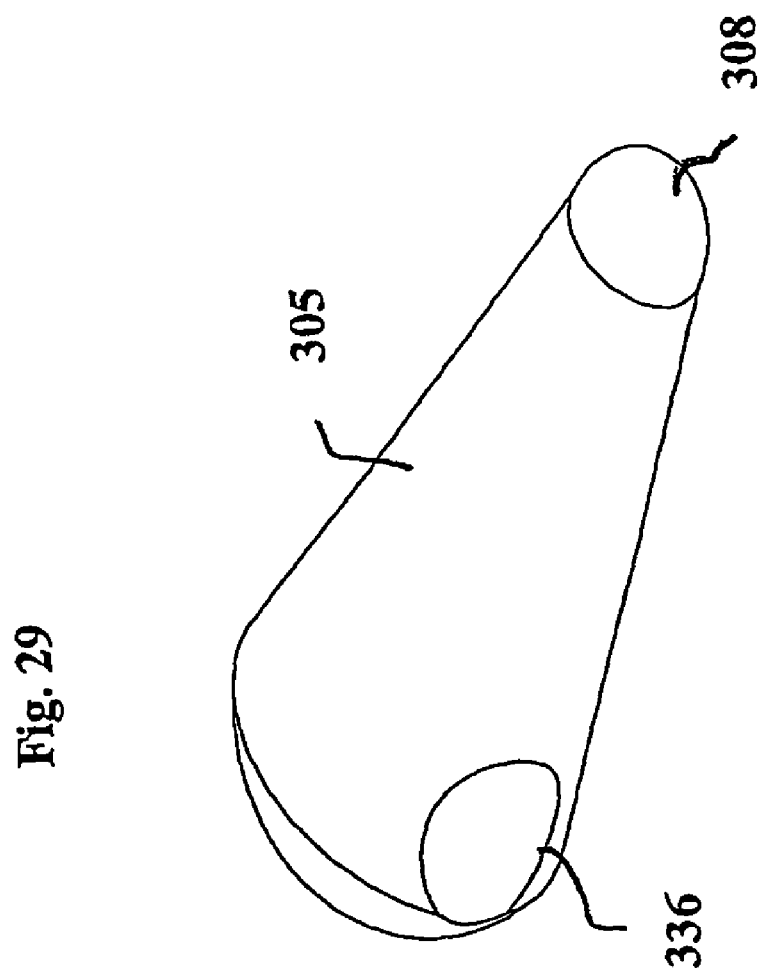
FIG. 29 is a perspective view of a pivot member of the fourth embodiment.
Figure 32:
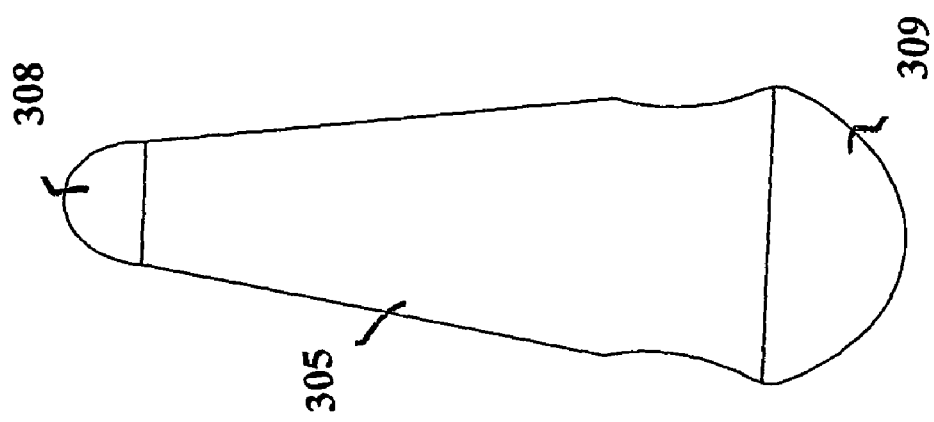
FIG. 32 is a side view of the pivot member of the fourth embodiment.
Figure 31:
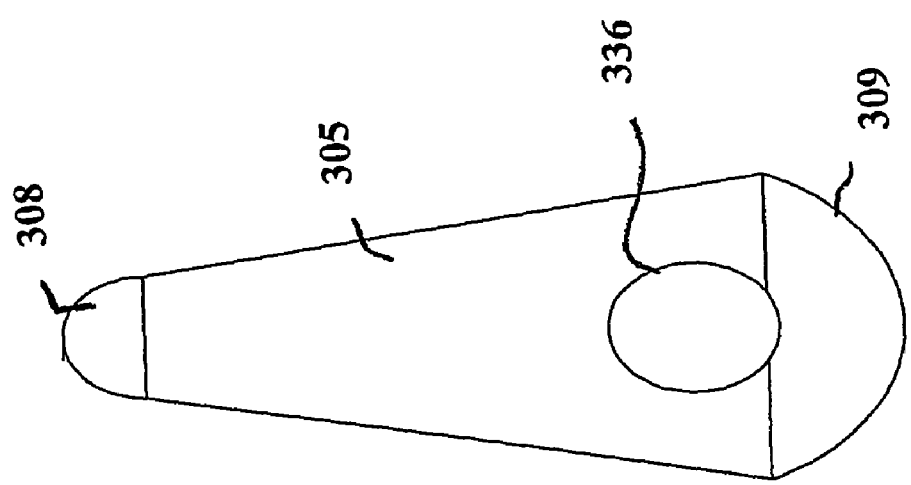
FIG. 31 is a front view of the pivot member of the fourth embodiment.
Figure 33:
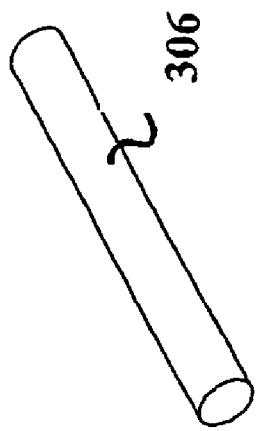
FIG. 33 is a perspective view of a pin used in the fourth embodiment.
Figure 34:
FIG. 34 is a side view of the pin of the fourth embodiment.
Figure 35:
FIG. 35 is a front view of the pin of the fourth embodiment.
Figure 37:
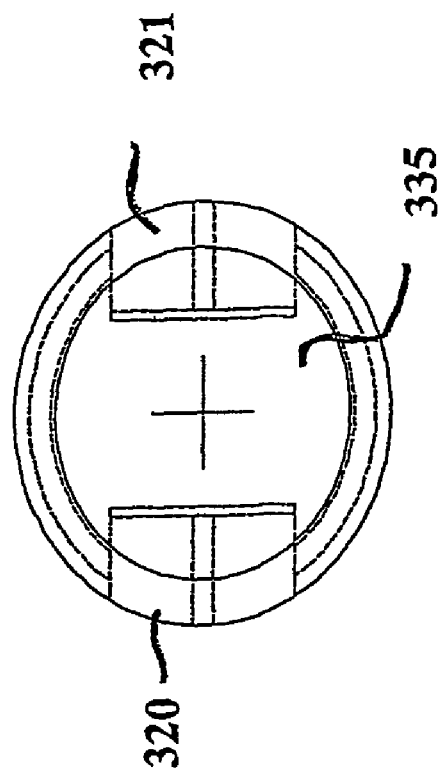
FIG. 37 is a plan view of the component shown in FIG. 36.

Another embodiment of a gauge 40 includes a read-out face as illustrated in FIG. 22. This embodiment differs from the above embodiments in that it utilises two separate plumb bobs 41 and 42 as opposed to a single plumb bob 3. In such an embodiment, the first and second plumb bobs 41 and 42 are separately mounted to the gauge body 43 so as to each hang under the influence of gravity. The first plumb bob 41 is mounted to the body 43 for rotation in the first plane about a first axis 44 and the second plumb bob 42 is mounted to the body 43 for rotation in the second plane about a second axis 45. The first axis 44 is orthogonal to the second axis 45. In use, the surgeon compares the position of the first plumb bob 41 against either markings 46 or 47 to determine the first angle. Similarly, the position of the second plumb bob 42 is compared against markings 48 or 49 to determine the second angle. This embodiment has the advantage of mechanical simplicity in comparison to gauges 1 as illustrated in FIGS. 1 to 8 since this embodiment does not require the provision of a universal joint 30.

A fourth embodiment of the invention is shown in FIGS. 23 to 47 inclusive. This preferred embodiment of the gauge 301 includes a body 302 with a plumb bob 303 mounted to the body 302. The plumb bob 303 hangs from the body 302 under the influence of a local gravitational field. More particularly, the plumb bob 303 is rotatable relative to the body 302 in both a first plane and a second plane, said planes being orthogonal to each other.

A universal joint 304 rotatably mounts the plumb bob 303 to the body 302. The universal joint 304 is composed of an elongate pivot member 305, best shown in FIGS. 29 to 32. The pivot member 305 is fixedly disposed on pin 306, which extends through aperture 336 provided in the pivot member 305. The pin 306 is fixedly disposed within apertures 337 and 338 provided upon the body 307. The pivot member 305 defines a hemispherical head 308 and a hemispherical base 309. The upper hemispherical head 308 is adapted to mate with a corresponding hemispherical cavity 310 provided in an upper component 311 of the plumb bob 303.

The diameter of the hemispherical head 308 is equal to the diameter of the corresponding hemispherical cavity 310. An excessively small diameter may promote an overly sensitive output for the gauge; in that the indicator needle 315 oscillates for an unacceptably long period before settling down to a steady reading. Conversely, an excessively large diameter will impart too much damping to the plumb bob, potentially causing an inaccurate reading. In the preferred embodiment this diameter is preferably greater than 1 mm, and less than 6 mm. More preferably, the diameter is greater than 2 mm, and less than 4 mm. The diameter utilised in the preferred embodiment is 3 mm, which has been found to impart an acceptable degree of damping to the movement of the plumb bob 303 relative to the body 302.

During assembly, the plumb bob 303 is rotatably mounted to the body 302 by placing the upper component 311 such that the cavity 310 either engages, or is directly proximate to, the head 308. A lower component 312 of the plumb bob 303 is disposed at or adjacent to the opposite end of the pivot member 305, such that the upper and lower components 311 and 312 mate with each other. More particularly, a recess 313 on the lower edge of the upper component 311 is adapted to mate with a flange 314 provided upon an upper edge of the lower component 312. The upper and lower components 311 and 312 are then joined to each other, for example by joining means such as soldering, gluing, or the like. This effectively seals the pivot member 305 within the plumb bob 303. Hence, when the gauge is in use and the pivot member 305 is oriented substantially vertically, the plumb bob 303 is free to rotate in two planes to allow the center of gravity of the plumb bob to assume a position immediately below the head 308. In doing so, the indicator needle 315 rotates to a position that allows two angles to be read against the two sets of marlings 316 and 317 in the manner outlined in detail with reference to previously described embodiments.

The internal dimensions of the cavity inside the plumb bob 303 in which the pivot member 305 is enclosed are chosen to ensure that when the plumb bob 303 hangs under gravity from the head 308, a minimal clearance gap is provided between the base 309 and the adjacent internal surface 335 of the lower component 312. This ensures that the plumb bob 303 only engages the pivot member 305 at its head 308, to allow the plumb bob to hang freely. That is, the type of joint used in this preferred embodiment may be termed a "singular pivot-point joint", wherein the head 308 of the pivot member 305 effectively functions as a "singular pivot point". The clearance gap is preferably minimal to ensure that the plumb bob cannot be displaced any significant distance away from its engagement with the head 308, as could happen for example if the gauge 301 is giggled up and down, or inadvertently dropped. A clearance gap of approximately 0.5 mm is utilised in the preferred embodiment. In other words, the minimal clearance gap ensures that the cavity 310 remains closely adjacent to the head 308, even if the gauge is giggled or dropped, and will therefore return to engagement with the head 308 when the gauge 301 is returned to its in-use orientation relative to gravity.

Cut-aways 318 and 319 are provided on opposite sides of the upper component 311 of the plumb bob 303 to allow the plumb bob 303 to rotate within its allowable range of movement without impacting upon the pin 306. For the same reason, further cut-aways 320 and 321 are provided upon the lower component 312 of the plumb bob 303.

The fourth embodiment of the gauge 301 is connectable to other surgical implements via connector 322, in the form of a bayonet-type connector. A female connector component 323 is disposed on a side of the body 302. This female connector component 323 includes a hollow cylinder 332 having a proximal end 324 that is attached to the body 302 and an open distal end 325 adapted to accept a male connector component 328. The open distal end 325 has two opposed channels 329 and 330, which respectively define two tracks into which a corresponding pair of prongs 326 and 327 projecting from the male connector component 328 may be inserted. To guard against mis-alignment of the gauge 301 relative to the surgical implement to which it is being connected, the tracks 329 and 330 and corresponding prongs 326 and 327 are of different sizes. Hence, there is only one relative orientation between the gauge 301 and the surgical implement that will allow both prongs to mate with both tracks. If mis-aligned by 180°, the larger prong 326 will not fit into the smaller channel 330.

The female connector component 323 includes resilient biasing means, in the form of a spring 331, that is disposed around the hollow cylinder so as to bear against the prongs 326 and 327 upon insertion of the male connector component 328 into the female connector component 323. This biases the prongs toward the distal end of the hollow cylinder. Hence, once the gauge 301 is rotated relative to the surgical implement to which it is being attached, the prongs 326 and 327 are displaced around the curves 333 and 334 in the tracks, at which point the resilient biasing forces the prongs into secure engagement with the ends 335 and 336 of the tracks, thereby connecting the gauge 301 to the surgical implement. Whilst connected, the end of the shaft 339 of the male connector component 328 is housed within the hollow cylinder 332.

To disconnect the gauge 301 from the male connector component 328 of the surgical implement, the user must displace the prongs 326 and 327 against the biasing force, then twist the gauge 301 relative to the surgical implement so as to displace the prongs 326 and 327 back around the curves 333 and 334, to allow the prongs to disengage from the open ends of the tracks 340 and 341.

Although the invention has been described with reference to specific embodiments, it will be appreciated by those skilled in the art that the invention may be embodied in many other forms.

The invention claimed is:

1. A gauge for use in a surgical procedure to determine a first angle in a first plane and a second angle in a second plane, said gauge comprising:
   a body;
   a plumb bob mounted to said body so as to hang under the influence of a local gravitational field, said plumb bob being rotatable relative to said body in both said first plane and said second plane so as to determine said first angle and said second angle respectively; and
   a first connector disposed on said body of said gauge; and
   a second connector including structure for attachment with a prosthetic component, said first connector and said second connector including corresponding structure for connection therebetween for mounting of said gauge between said prosthetic component and a predefined site of a patient to allow correlation between the predefined site of said patient and positioning of said prosthetic component.

2. The gauge according to claim 1, wherein a universal joint rotatably mounts said plumb bob to said body.

3. The gauge according to claim 2, wherein said universal joint is any one of: a ball joint; a singular pivot-point joint; an eye end joint; a tie rod end joint; or a rose joint.

4. The gauge according to claim 1, wherein said first plane is orthogonal to said second plane.

5. The gauge according to claim 1, wherein said plumb bob includes a pointer.

6. The gauge according to claim 5, wherein said body includes markings disposed adjacent said pointer.

7. The gauge according to claim 6, wherein a first sub-set of said markings corresponds to angular increments of said first angle and a second sub-set of said markings corresponds to angular increments of said second angle.

8. The gauge according to claim 1, wherein said surgical procedure is the insertion of an acetabular cup into a reamed acetabulum during hip replacement surgery, wherein the second connector is attached to the acetabular cup.

9. The gauge according to claim 8, wherein said first angle corresponds to an aversion of said acetabular cup relative to the reamed acetabulum.

10. The gauge according to claim 8, wherein said second angle corresponds to an abduction of said acetabular cup relative to the reamed acetabulum.

11. The gauge according to claim 1, wherein movement of the plumb bob relative to the body is damped.

12. A gauge for use in a surgical procedure to determine a first angle in a first plane and a second angle in a second plane, said gauge comprising:
   a body;
   a first plumb bob mounted to said body so as to hang under the influence of a local gravitational field, said first plumb bob being rotatable relative to said body in said first plane so as to determine said first angle;
   a second plumb bob mounted to said body so as to hang under the influence of a local gravitational field, said second plumb bob being rotatable relative to said body in said second plane so as to determine said second angle; and
   a first connector disposed on said body of said gauauge, and
   a second connector including structure for attachment with a prosthetic component, said first connector and second connector including corresponding structure for connection therebetween for connection of said gauge between said prosthetic component and a predefined site of a patient.

13. The gauge according to claim 12, wherein said first plumb bob is mounted to said body for rotation about a first axis and the second plumb bob is mounted to said body for rotation about a second axis, whereby said first axis is orthogonal to said second axis.

* * * * *